US010405975B2

(12) United States Patent
Anderson-Cunanan et al.

(10) Patent No.: US 10,405,975 B2
(45) Date of Patent: *Sep. 10, 2019

(54) CULTURED CELL LEAFLET MATERIAL

(71) Applicant: Boston Scientific SciMed, Inc., Maple Grove, MN (US)

(72) Inventors: Crystal Marie Anderson-Cunanan, San Jose, CA (US); Katherine Cora Fazackerley, San Mateo, CA (US); Michael Eppihimer, Franklin, MA (US); Shannon Smith Kenwood, Winthrop, MA (US); Natalia P. Sushkova, Chestnut Hill, MA (US); Karen Suzanne Lavery, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/272,747

(22) Filed: Sep. 22, 2016

(65) Prior Publication Data

US 2017/0100237 A1 Apr. 13, 2017

Related U.S. Application Data

(60) Provisional application No. 62/238,222, filed on Oct. 7, 2015.

(51) Int. Cl.
*A61F 2/24* (2006.01)
*A61L 27/36* (2006.01)
(Continued)

(52) U.S. Cl.
CPC .......... *A61F 2/2415* (2013.01); *A61F 2/2412* (2013.01); *A61F 2/2418* (2013.01);
(Continued)

(58) Field of Classification Search
CPC .............. A61L 31/16; A61L 2300/216; A61L 2300/414; A61L 2300/604; A61L 2430/02;
(Continued)

(56) References Cited

U.S. PATENT DOCUMENTS

| 6,409,759 B1* | 6/2002 | Peredo ................. A61F 2/2412 623/2.13 |
| 10,195,024 B2* | 2/2019 | Anderson-Cunanan ..................... A61F 2/2415 |

(Continued)

FOREIGN PATENT DOCUMENTS

| WO | 9825549 | 6/1998 |
| WO | 2017062198 | 4/2017 |

(Continued)

OTHER PUBLICATIONS

Billiar, Kristen L. et al., "Biaxial Mechanical Properties of the Native and glutaraldehyde—Treated Aortic Valve Cusp: Part II—A Structural Constitutive Model," Journal of Biomechanical Engineering (2000) vol. 122, pp. 327-335.

(Continued)

*Primary Examiner* — Ann Schillinger
(74) *Attorney, Agent, or Firm* — Pauly, DeVries Smith & Deffner LLC

(57) ABSTRACT

A prosthetic heart valve provided herein can include a cultured cell tissue leaflet. In some cases, a prosthetic heart valve can include a plurality of leaflets secured together and retained within the expandable tubular member. The cultured cell tissue can be obtained by culturing fibroblast cells, smooth muscle cells, or a combination thereof to form a sheet of cultured cells and chemically cross-linking the fibroblast cells while under tension. In some cases, the (Continued)

cultured cell tissue can be radially tensioned. In some cases, the cultured cell tissue can be bi-axially tensioned.

18 Claims, 12 Drawing Sheets

(51) Int. Cl.
    *A61L 27/38* (2006.01)
    *A61L 27/50* (2006.01)
    *C12N 5/077* (2010.01)
    *C12M 3/00* (2006.01)
(52) U.S. Cl.
    CPC ....... *A61L 27/3687* (2013.01); *A61L 27/3804* (2013.01); *A61L 27/3826* (2013.01); *A61L 27/3873* (2013.01); *A61L 27/3886* (2013.01); *A61L 27/3895* (2013.01); *A61L 27/507* (2013.01); *C12N 5/0656* (2013.01); *C12N 5/0661* (2013.01); *A61L 2430/20* (2013.01); *C12M 21/08* (2013.01); *C12N 2502/1347* (2013.01); *C12N 2527/00* (2013.01); *C12N 2537/10* (2013.01)
(58) Field of Classification Search
    CPC .. A61L 2430/38; A61L 27/24; A61L 27/3691; A61L 27/54; A61L 31/14; A61L 31/148
    See application file for complete search history.

(56) References Cited

U.S. PATENT DOCUMENTS

| | | | |
|---|---|---|---|
| 10,231,830 B2* | 3/2019 | Swanson | A61F 2/2415 |
| 2002/0094573 A1* | 7/2002 | Bell | A61L 27/3604 |
| | | | 435/398 |
| 2002/0103542 A1* | 8/2002 | Bilbo | A61L 15/40 |
| | | | 623/23.72 |
| 2003/0229394 A1 | 12/2003 | Ogle et al. | |
| 2004/0078090 A1* | 4/2004 | Binette | A61L 27/36 |
| | | | 623/23.76 |
| 2005/0143809 A1 | 6/2005 | Salahieh et al. | |
| 2005/0222661 A1 | 10/2005 | Case et al. | |
| 2006/0159722 A1 | 7/2006 | Braithwaite et al. | |
| 2006/0253188 A1 | 11/2006 | Case et al. | |
| 2007/0037283 A1 | 2/2007 | Patel et al. | |
| 2007/0162103 A1 | 7/2007 | Case et al. | |
| 2007/0254005 A1* | 11/2007 | Pathak | A61K 35/12 |
| | | | 424/423 |
| 2009/0138078 A1 | 5/2009 | Paul, Jr. et al. | |
| 2009/0187241 A1 | 7/2009 | Melsheimer et al. | |
| 2009/0216338 A1 | 8/2009 | Gingras et al. | |
| 2014/0277416 A1 | 9/2014 | Matheny et al. | |
| 2016/0296323 A1 | 10/2016 | Wulfman et al. | |
| 2017/0100238 A1 | 4/2017 | Anderson-Cunanan et al. | |
| 2017/0128201 A1 | 5/2017 | Swanson et al. | |

FOREIGN PATENT DOCUMENTS

| | | |
|---|---|---|
| WO | 2017062199 | 4/2017 |
| WO | 2017083183 | 5/2017 |

OTHER PUBLICATIONS

"International Search Report and Written Opinion," for PCT Application PCT/US2016/053680 dated Dec. 16, 2016 (12 pages).
"International Search Report and Written Opinion," for PCT Application PCT/US2016/053682 dated Jan. 3, 2017 (13 pages).
"International Search Report and Written Opinion," for PCT Application PCT/US2016/060449 dated Feb. 24, 2017 (12 pages).
Kelm, J. M. et al., "A Novel Concept for Scaffold-Free Vessel Tissue Engineering: Self-Assembly of Microtissue Building Blocks," Journal of Biotechnology, 148 (2010): pp. 46-55.
Cardinal, Kristen O. et al., "Tissue-Engineered Vascular Grafts as in Vitro Blood Vessel mimics for the Evaluation of Endothelialization of Intravascular Devices," Tissue Eng. 12, 3431-3438, 2006 (8 pages).
Gauvin, R. et al., "Dynamic Mechanical Stimulations Include Anisotropy and Improve the Tensile Properties of Engineered Tissues Produced Without Exogenous Scaffolding," Acta. Biomater. 7, 3294-3301, 2011 (8 pages).
Kalejs, et al., "St. Jude Epic Heart Valve Bioprostheses Versus Native Human and Porcine Aortic Valves—Comparison of Mechanical Properties," Interactive Cardiovascular and Thoracic Surgery 8 (2009) 553-557.
Kelm, J. M. et al., "Scaffold-Free Cell Delivery for Use in Regenerative Medicine," Adv. Drug Deliv. Rev. 62, 753-764, 2010 (12 pages).
L'Heureux, N. et al., "A Completely Biological Tissue-Engineered Human Blood Vessel," FASEB J. 12, 47-56, 1998 (10 pages).
Milleret, Vincent et al., "Tuning Electrospinning Parameters for Production of 3D-Fiber-Fleeces with Increased Porosity for Soft Tissue Engineering Applications," Eur. Cell. Mater. 21, 286-303, 2011 (18 pages).
Schellenberg, Anne et al., "3D Non-Woven Polyvinylidene Fluoride Scaffolds: Fibre Cross Section and Texturizing Patterns Have Impact on Growth of Mesenchymal Stromal Cells," PLOS ONE 9(4) e94353, 2014 (9 pages).
"Non-Final Office Action," for U.S. Appl. No. 15/272,772 dated Mar. 2, 2018 (17 pages).
"Final Office Action," for U.S. Appl. No. 15/272,772 dated Jun. 5, 2018 (10 pages).
"International Preliminary Report on Patentability," for PCT Application No. PCT/US2016/053680 dated Apr. 19, 2018 (8 pages).
"International Preliminary Report on Patentability," for PCT Application No. PCT/US2016/053682 dated Apr. 19, 2018 (8 pages).
"International Preliminary Report on Patentability," for PCT Application No. PCT/US2016/060449 dated May 24, 2018 (8 pages).
"Non-Final Office Action," for U.S. Appl. No. 15/340,242 dated Apr. 10, 2018 (22 pages).
"Response to Non-Final Office Action," for U.S. Appl. No. 15/340,242 dated Apr. 10, 2018 and filed Jun. 18, 2018 (11 pages).
Notice of Allowance for U.S. Appl. No. 15/340,242 dated Oct. 26, 2018 (9 pages).
Response to Communication Pursuant to Rules 161(1) and 162 EPC for European Patent Application No. 16777878.6 filed Nov. 29, 2018 (5 pages).
Response to Communication Pursuant to Rules 161(1) and 162 EPC for European Patent Application No. 16778164.0 filed Dec. 10, 2018 (11 pages).
Response to Communication Pursuant to Rules 161(1) and 162 EPC for European Patent Application No. 16804954.2 filed Dec. 19, 2018 (10 pages).
Final Office Action for U.S. Appl. No. 15/340,242 dated Jul. 26, 2018 (14 pages).
Notice of Allowance for U.S. Appl. No. 15/272,772 dated Sep. 24, 2018 (7 pages).
Response to Final Rejection dated Jun. 5, 2018, for U.S. Appl. No. 15/272,772 submitted via EFS-Web on Aug. 31, 2018, 8 pages.
Response to Final Rejection dated Jul. 26, 2018 for U.S. Appl. No. 15/340,242 submitted via EFS-Web on Sep. 26, 2018, 9 pages.
"Communication Pursuant to Article 94(3) EPC," for European Patent Application No. 16777878.6 dated Apr. 29, 2019 (6 pages).

* cited by examiner

CULTURED CELL LEAFLET MATERIAL

This application claims the benefit of U.S. Provisional Application No. 62/238,222, filed Oct. 7, 2015, the contents of which are herein incorporated by reference.

FIELD

This document provides leaflets made out of cultured cell material.

BACKGROUND

Heart valve surgery can be used to repair or replace diseased heart valves. For example, heart valve replacement may be indicated when there is a narrowing of the native heart valve, commonly referred to as stenosis, or when the native valve leaks or regurgitates. The repair or replacement of diseased heart valves can include, for example, the introduction of a prosthetic heart valve that includes biological tissue heterologous to the patient (e.g., a heterograft or xenograft). A common biological tissue used to make prosthetic heart valves is pericardial tissue, typically bovine or porcine. Attempts to grow life cell leaflets from stem cells, however, have proven inadequate for the replacement of heart valves.

SUMMARY

Prosthetic heart valves provided herein use cultured cell tissue as the leaflet material. The cultured cells leaflet provided herein is produced by culturing fibroblast, smooth muscle cells, or a combination of these cell to form a tissue sheet, chemically cross-linking the sheet of cultured cells while under tension to fix the sheet, and cutting a heart valve leaflet from the fixed sheet of cultured cells.

In Example 1, a prosthetic heart valve can include a plurality of leaflets secured together and retained within the expandable tubular member where each leaflet includes radially or biaxially oriented and chemically cross-linked cultured cell tissue material.

In Example 2, the prosthetic heart valve of Example 1 where the cultured cell material is cultured from fibroblast cells, preferably dermal fibroblast cells, more preferably bovine dermal fibroblast cells.

In Example 3, the prosthetic heart valve of Example 1 or 2 where the cultured cell material is cultured from smooth muscle cells, preferably bovine smooth muscle cells.

In Example 4, the prosthetic heart valve of Example 1 where the cultured cell material is cultured from a mixture of fibroblasts and smooth muscle cells, preferably at a ratio of between 20:80 and 80:20, preferably the mixture includes of bovine fibroblasts and bovine smooth muscle cells.

In Example 5, the prosthetic heart valve of one of Examples 1-4 where the cultured cell tissue is cross-linked with glutaraldehyde.

In Example 6, the prosthetic heart valve of one of Examples 1-5 where the cultured cells are cultured for at least 3 weeks, preferably at least 4 weeks, more preferably at least 5 weeks, and even more preferably at least 6 weeks.

In Example 7, the prosthetic heart valve of one of Examples 1-6 where the cultured cell tissue has a thickness of between 50 micrometers and 300 micrometers, preferably between 75 micrometers and 200 micrometers.

In Example 8, the prosthetic heart valve of one of Examples 1-7 where the cultured cell tissue has a percentage of elongation at 500 kPa of between 6.5% and 8.5%.

In Example 9, the prosthetic heart valve of one of Examples 1-8 where the cultured cell tissue has a percentage of elongation at 1 MPa of between 10.5% and 13.5%.

In Example 10, the prosthetic heart valve of one of Examples 1-9 where the cultured cell tissue has an ultimate tensile strength of between 4 MPa and 6.5 MPa.

In Example 11, the prosthetic heart valve of one of Examples 1-10 where the cultured cell tissue has a shrinkage temperature of between 83.8° C. and 84.6° C.

In Example 12, the prosthetic heart valve of one of Examples 1-11 where the cultured cell tissue has a moisture content of between 80% and 88%.

In Example 13, the prosthetic heart valve of one of Examples 1-12 where the leaflets consist of radially or biaxially oriented and fixed cultured cell material.

In Example 14, a method of forming a cultured cell leaflet can include: (a) obtaining fibroblast cells, smooth muscle cells, or a combination thereof; (b) culturing the cells on a frame to produce a sheet of cultured cells; (c) applying tension to the sheet of cultured cell tissue; (d) contacting the cultured cell tissue with a chemical cross-linker for at least 10 minutes while tension is applied to the sheet of cultured cell tissue; and (e) cutting out a leaflet from the sheet, the leaflet comprising a body portion and two sleeve portions.

In Example 15, the method of Example 14 where the cultured cells comprise a mixture of fibroblast cells and smooth muscle cells in a ratio of between 20:80 and 80:20.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
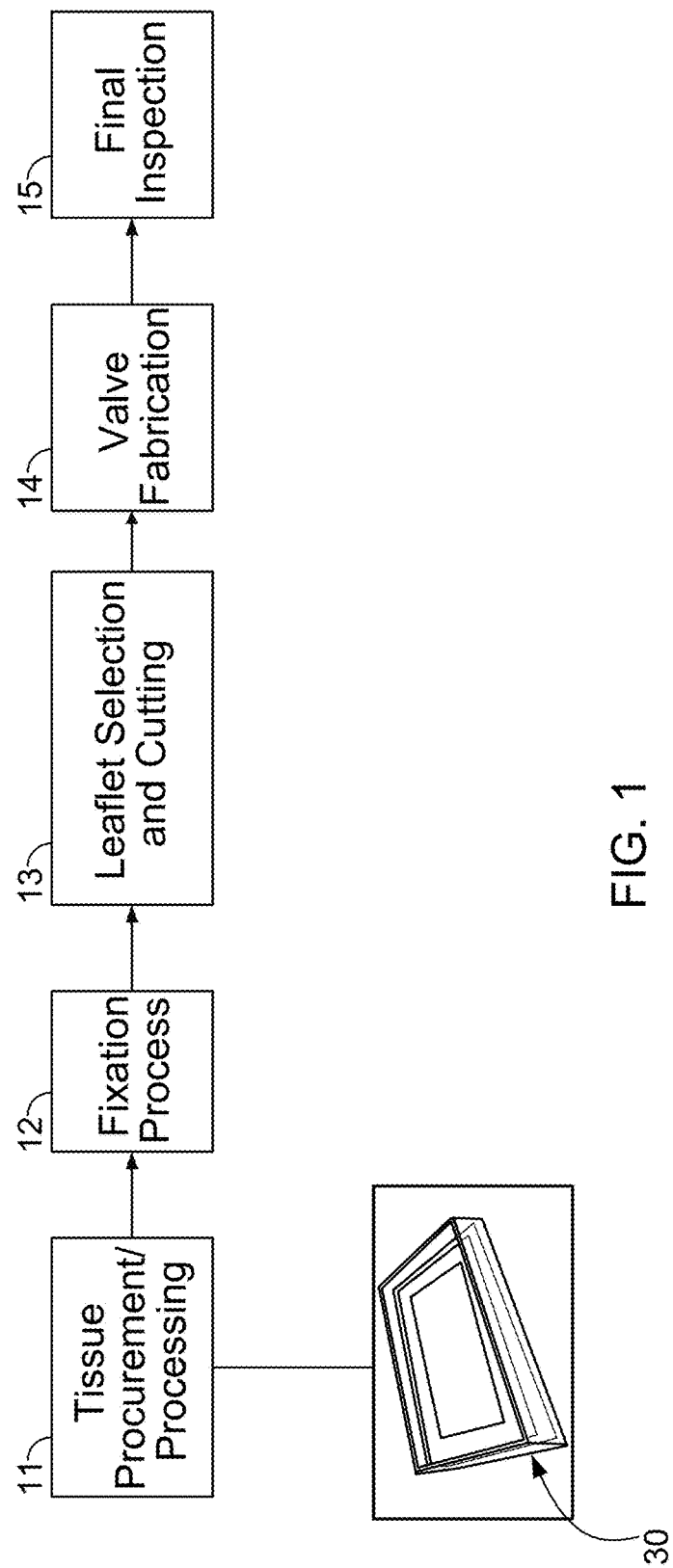
FIG. 1 is flow chart depicting an exemplary method for producing a heart valve using cultured cell tissues.

Prosthetic heart valves provided herein include biaxial tensioned and fixed cultured cell tissue leaflets. Prosthetic heart valves have typically used bovine or porcine pericardium tissue leaflets, but controlling the properties of these natural tissues can be difficult. For example, diseases in the animals can result in defective tissue properties. Moreover, the tissue can have uneven mechanical properties. Additionally, proving that the animal tissue is free of disease or meeting certain governmental regulations tracking the health conditions of animals raised to produce the natural tissue can be difficult and expensive. Additionally, an outbreak of disease among herds of animals raised to produce biological tissues for medical implants can result in shortages of usable biological tissue for medical devices.

Prior attempts to grow heart valves out of live cells have proven insufficient in developing the appropriate mechanical properties for the heart valve leaflets. Merely having cells grown into the shape of leaflets is insufficient to produce a replacement heart valve having the mechanical and biological properties needed for long term in vivo use. Cultured cell tissue leaflets as provided herein, however, can consistently produce leaflets having appropriate biological and mechanical properties. In some cases, cultured cell tissue leaflets provided herein can be subjected to radial or biaxial forces during growth. In some cases, cultured cell tissue leaflets provided herein can be subjected to radial or biaxial forces during fixation. In some cases, the cultured cell tissue can be produced using bovine dermal fibroblasts (BDFs) and/or smooth muscle cells (SMCs) to produce the tissue sheets in vitro. Upon reaching the desired thickness, these sheets can be fixed and cross-linked to preserve a desired extra cellular matrix ("ECM") protein structure. Heart valve leaflets may be cut from these sheets and integrated into the current system.

As will be discussed below, culturing processes provided herein can produce sheets of cultured cells having uniform thicknesses and uniform mechanical properties. In some cases, radial or biaxially tensioned and fixed cultured cell tissue leaflets provided herein can have a thickness of between 50 micrometers and 300 micrometers. In some cases, radial or biaxially tensioned and fixed cultured cell tissue leaflets provided herein can have thickness of between 100 micrometers and 200 micrometers. In some cases, radial or biaxially tensioned and fixed cultured cell tissue leaflets provided herein can have a maximum thickness of between 130 micrometers and 150 micrometers. In some cases, sheets of cultured cells can be grown under tension and fixed by applying a cross-linking chemical (e.g., glutaraldehyde) to the tissue while the tissue remains connected to a frame used for growing the tissue. In some cases, sheets of cultured cells can be placed under additional tension prior to applying a cross-linking chemical (e.g., glutaraldehyde) to the tissue.

In some cases, the frame can supply radial tension to the cultured cell tissue. In some cases, the cultured cell tissue can be bi-axially tensioned. In some cases, the cultured cell tissue is biaxially tensioned by applying a stress load of at least 0.1 N to stretch the cultured cell tissue along two intersecting axes. In some cases, the cultured cell tissue is biaxially tensioned by applying a stress load of between 0.1 N and 2 N to stretch the cultured cell tissue along two intersecting axes. In some cases, the cultured cell tissue is biaxially tensioned by applying a stress load of between 0.5 N and 1 N to stretch the cultured cell tissue along two intersecting axes.

The cultured cell tissue can be chemically cross-linked while under tension to prevent recoil of the cultured cell tissue after the tension is released. In some cases, biaxially or radially tensioned and fixed cultured cell tissue leaflets provided herein can have a percentage of elongation at 500 kPa of between 6.5% and 8.5%. In some cases, biaxially or radially tensioned and fixed cultured cell tissue leaflets provided herein can have a percentage of elongation at 1 MPa of between 10.5% and 13.5%. In some cases, biaxially or radially tensioned and fixed cultured cell tissue leaflets provided herein can have an ultimate tensile strength of between 4 MPa and 6.5 MPa. In some cases, biaxially or radially tensioned and fixed cultured cell tissue leaflets provided herein can have a shrinkage temperature of between 83.8° C. and 84.6° C. In some cases, biaxially or radially tensioned and fixed cultured cell tissue leaflets provided herein can have a moisture content of between 80% and 88%. Additionally, the properties can be uniform regardless of the orientation of the tensioned and fixed cultured cell tissue. Fixed cultured cell tissue can provide a comparable material for prosthetic heart valve leaflets because of the consistency of the material properties. Methods, devices, and systems provided herein can provide reliable and consistent mechanical properties for cultured cell tissue leaflets used in prosthetic heart valves.

A sheet of cultured cells can be grown using any suitable method. In some cases, a sheet of cultured cells can be grown by isolating fibroblast cells and/or smooth muscle cells and allowing them to be cultured for between 3 and 12 weeks within a fixed frame. In some cases, the frame is arranged in a substantially rectangular configuration so that the resulting sheet of cultured cells has a substantially rectangular shape. In some cases, the frame is arranged in a circular ring configuration. In some cases, the frame is suitably rigid such that it is adapted to retain a planar configuration despite contractive forces from the tissue as it grows. In some cases, weights and/or grips can be applied to the frame to ensure that it retains its shape during tissue growth. In some cases, a frame can include paper. In some cases, the frame can have a porous structure to encourage tissue ingrowth. In some cases, a frame having growth media applied thereto can have fibroblast cells applied to it and be placed in a culture plate to allow for growth of the fibroblast cells. In some cases, the cultured sheet can consist essentially of cultured cells.

The cells can be from any suitable donor. In some cases, the cells can be bovine dermal fibroblast cells and/or smooth muscle cells. The fibroblast and/or smooth muscle cells can be from any suitable animal. In some cases, the cells can be bovine, porcine, equine, goat, or sheep. In some cases, the cells can be human dermal fibroblast cells and/or human smooth muscle cells. In some cases, the cells can be obtained from the intended patient.

FIG. 1 is a flow chart depicting the overall process of incorporating cultured cell tissue into a prosthetic heart valve. The first step 11 fibroblast and/or smooth muscle cells are grown into a sheet 30 of cells. In some cases, cells can be obtained from a dermal biopsy and arterial resections. In some cases, the fibroblast cells can be bovine cells. Fibroblast can be isolated from dermal tissue samples and arteries using any suitable isolation technique known in the art. Isolated fibroblast and/or smooth muscle cells can then be expanded to form a larger population of cells. The fibroblast and/or smooth muscle cells can be tested to ensure that they are free of disease. The cells can then be applied to a frame in a culture tray and grown for at least 3 weeks. In some cases, fibroblast cells alone are cultured into a sheet. In some cases, smooth muscle cells are cultured into a sheet. In some cases, a combination of smooth muscle cells and fibroblast cells are cultured together to form a sheet. In some cases, a sheet of cultured cells can include a ratio of between 20:80 and 80:20 of fibroblast cells to smooth muscle cells. In some cases, fibroblasts and smooth muscle are applied to the frame in a 1:1 ratio.

Figure 3:
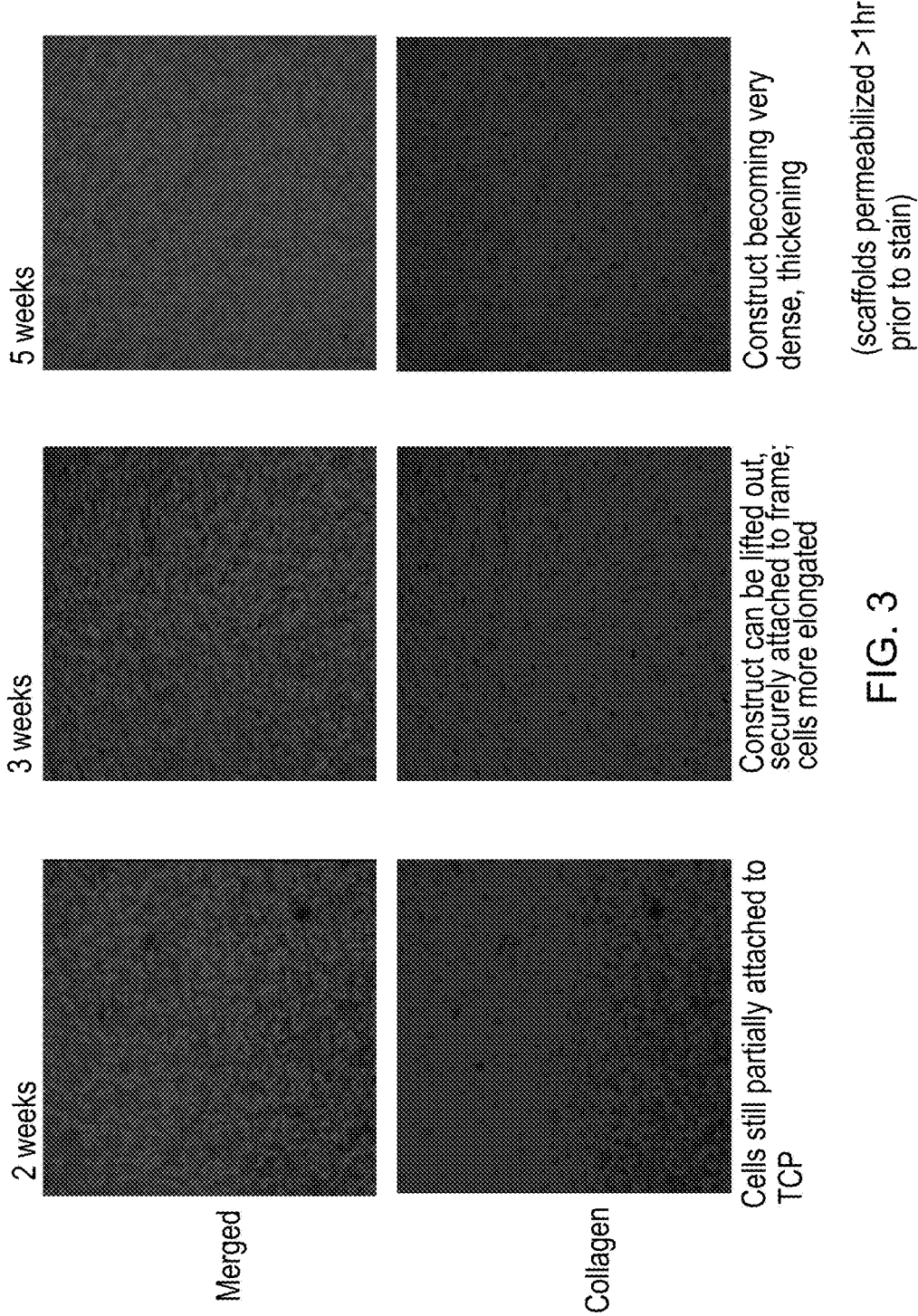
FIG. 3 depicts the growth of cultured bovine dermal fibroblast cells on a growth media over time.

FIG. 3 depicts the growth of cultured fibroblast cells over time. The first row of pictures includes dyes that show the collagen and the nuclei at 2 weeks, 3 weeks, and 5 weeks. The bottom row shows just the collagen at 2 weeks, 3 weeks, and 5 weeks. At two weeks, the cells are still partially attached to the transfer paper frame. At three weeks, the sheet of cultured cells can be lifted out of the culture tray. At three weeks, the thickness of the cultured cell sheet can be between 30 and 50 micrometers. At four weeks, the thickness of the cultured cell sheet can be between 90 and 110 microns. At five weeks, the thickness of the cultured cell sheet can be between 130 and 150 microns. Alternatively, sheets of cultured cells can be formed using a bioreactor.

Figure 2:
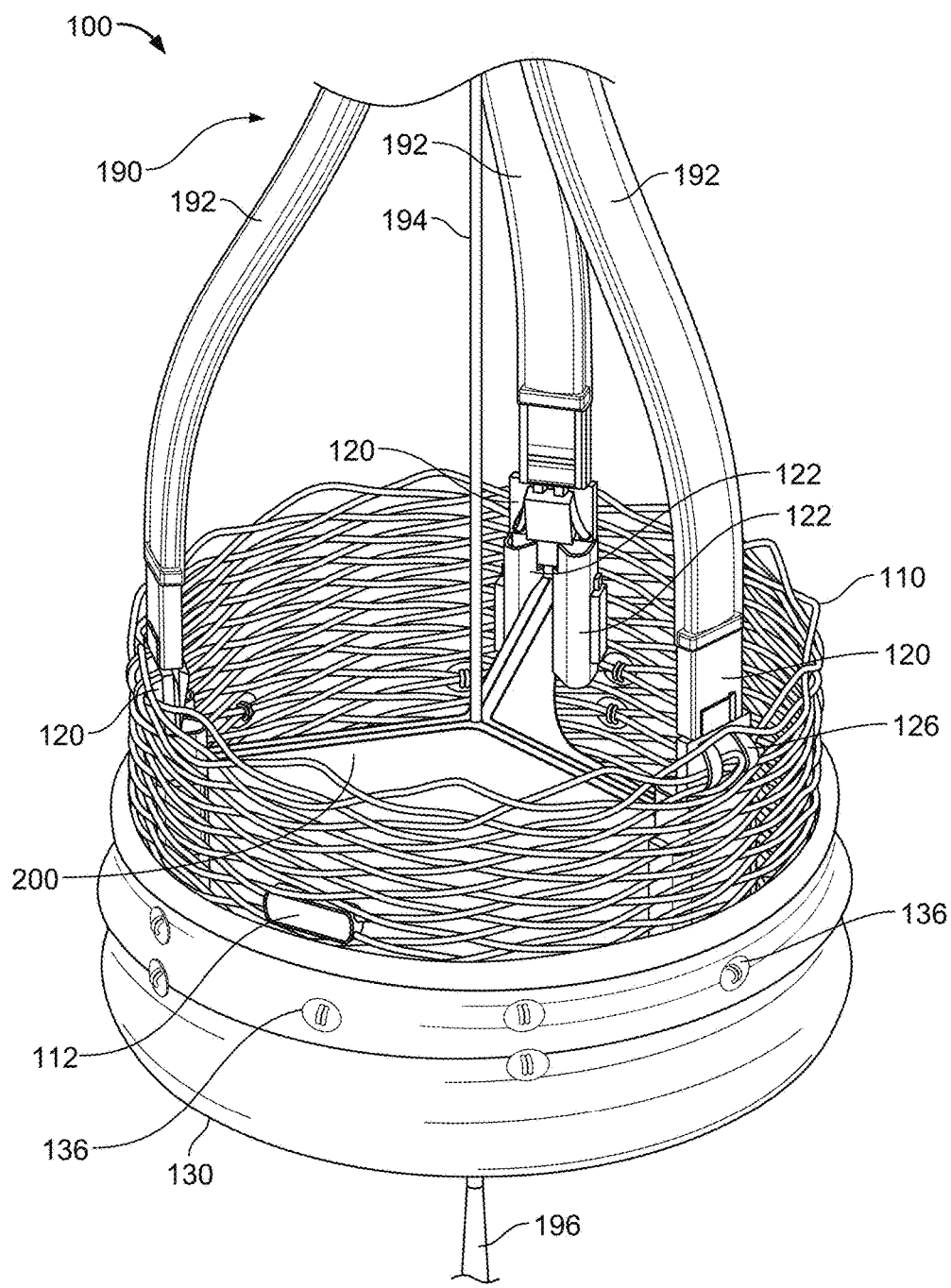
FIG. 2 is an exemplary prosthetic heart valve.

After obtaining the cultured cell sheet after at least 3 weeks of cell growth, the cultured cell can be fixed in step 12 while under biaxial or radial tension, which is described below. In step 13, leaflets having a predetermined shape are cut from the fixed cultured cell tissue, and suitable leaflets selected for use in a prosthetic heart valve, which is described below in connection to FIGS. 5 and 6. In step 14, a prosthetic heart valve is fabricated using one or more of the cut leaflets. In step 15, prosthetic heart valves can be inspected and/or tested to ensure that they meet specifications. In some cases, a prosthetic heart valve can be sterilized before or after inspection. FIG. 2 depicts an exemplary prosthetic heart valve. In some cases, three leaflets including the biaxially or radially oriented and fixed cultured cell material can be stitched to a frame and/or to each other to form a prosthetic heart valve.

Processes provided herein for cultured cell tissue modification can use one or more of the steps of fixing the tissue. In some cases, a sheet of cultured cell tissue is fixed with a chemical cross-linker when attached to a growth frame, with or without moving the cultured cell tissue from the growth chamber (e.g., a petri dish). In some cases, a sheet of cultured cell tissue can be additionally tensioned prior to or during fixation using a chemical cross-linker. In some cases, a sheet of cultured cell tissue can optionally be cut to a desired size or shape to simplify the tissue modification processes. In some cases, the sheet of cultured cell tissue can be substantially rectangular or substantially circular. In some cases, the cultured cell tissue can have an initial thickness of between 50 and 300 micrometers.

Figure 4:
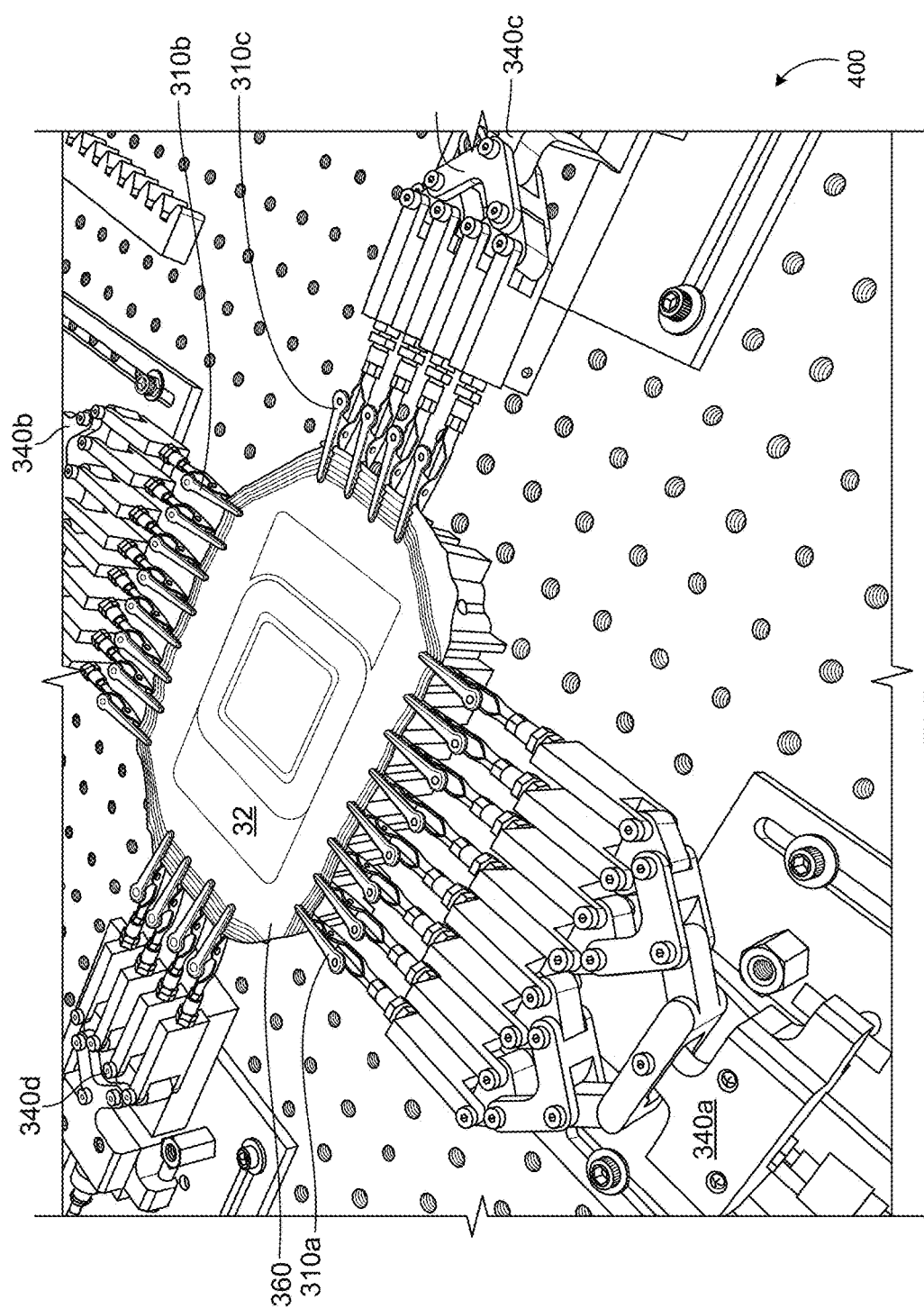
FIG. 4 illustrates a stretching machine for applying tension to the sheet of cultured cells.

In some cases, the cultured cell sheet is tensioned during the growth process and retains that tensioning during a fixation process. In some cases, additional tension can be applied to the cultured cell sheet. For example, a plurality of grippers can be arranged around a sheet of cultured cell tissue placed over a frame and stretched to tension the sheet of cultured cell tissue. FIG. 4 depicts an exemplary tissue stretching machine 400, which can include a plurality of force actuators 340a, 340b, 340c, and 340d, each adapted to apply a stress load to sides of the sheet via grippers 310a, 310b, 310c, and 310d, each secured to edge portions of sheet 32. Sheet 32 can be positioned over frame 360, such that after tensioning, sheet 32 can be stapled to frame 360 so that the sheet can be chemically cross-linked while under biaxial tension.

Figure 5:
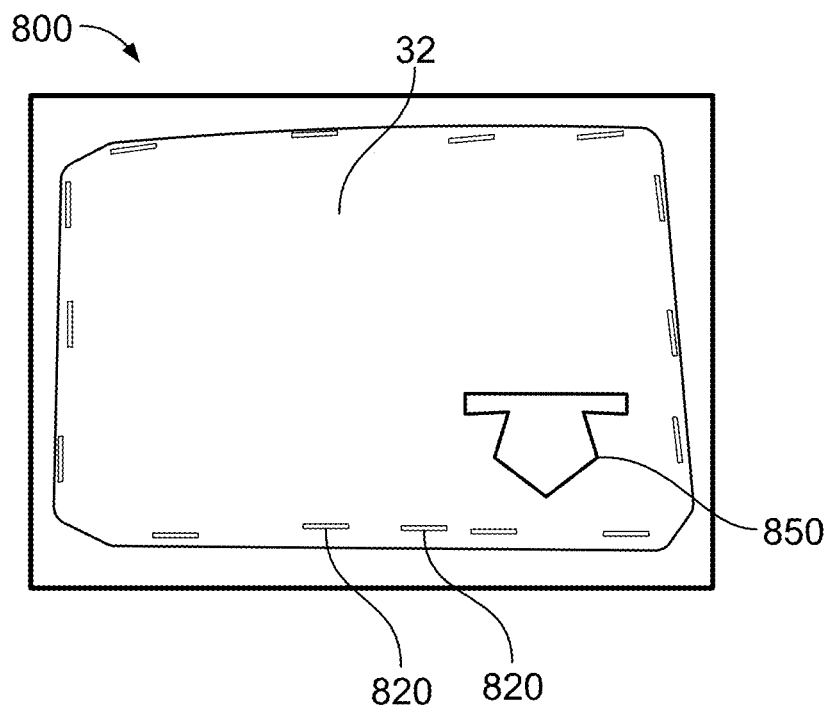
FIG. 5 depicts a frame for securing biaxially tensioned cultured cell tissue for treatment and cutting of leaflets.
Figure 6:
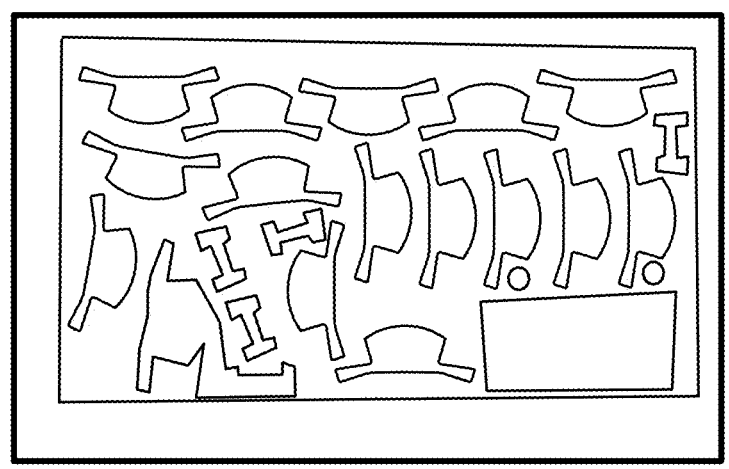
FIG. 6 depicts a platens for flattening the cultured cell tissue prior to stretching and cross-linking.

The tensioned sheet of cultured cell tissue can be captured on a frame, such as shown in FIG. 5, to retain the tensioning for further processing. For example, as shown in FIG. 5, tensioned sheet 32 can be secured on the frame by a plurality of staple 820 to create a tissue-frame assembly 800. The tensioned sheet is chemically cross-linked to fix the biological tissue. For example, glutaraldehyde is a suitable chemical cross-linker. In some cases, tissue-frame assembly 800 can be placed in a solution including 0.6 wt % glutaraldehyde for at least 10 minutes to chemically cross-link the cultured cell tissue.

FIG. 2 illustrates an exemplary prosthetic heart valve 100 provided herein, which can use leaflets 200 including tensioned and fixed cultured cell material provided herein. FIG. 2 is a perspective view of prosthetic heart valve 100 connected to a deployment device 190. As shown, prosthetic heart valve 100 includes an expandable member 110 (e.g., a braided stent), three biaxially oriented and fixed cultured cell leaflets 200, three anchor elements 120 that secure sleeve portions 216 of leaflets 200 to expandable member 110, and a tubular seal 130 secured around a blood inflow end of prosthetic heart valve 100. To facilitate better understanding, FIG. 2 does not show components that are located underneath tubular seal 130. Anchor elements 120 can include post leg compression elements 122 and clamping support structures 126 adapted to provide support along opposite sides of the sleeve portions 216. Expandable member 110 shown in FIG. 2 is a braided stent (which can also be described as a braided anchor element), which is adapted to transition between a restricted state having a smaller diameter and an expanded state having a larger diameter. Expandable member 110 can be self-expanding, mechanically expanded, or a combination thereof. In some cases, one or more radiopaque markers can be secured to prosthetic heart valves provided herein. As shown, expandable member 110 includes a radiopaque marker 112. Any suitable radiopaque material (such as platinum, palladium, gold, tantalum, or alloys thereof) can be used as the radiopaque material in radiopaque marker 112. One or more radiopaque markers can be used with an imaging system to help a physician ensure that a valve is set in an appropriate location. In some cases, prosthetic heart valves provided herein include at least three radiopaque markers. Expandable member 110 can have any suitable structure, arrangement, or material. In some cases, expandable member 110 can include a braided wire stent. For example, U.S. Publication Number 2005/0143809, titled, "Methods and Apparatus for Endovascularly Replacing a Heart Valve," and filed on Nov. 5, 2004, which is herein incorporated by reference for its disclosure of possible structures and materials for a braided wire stent, discloses a braided wire stent. In some cases, expandable member 110 includes a shape memory material (e.g., a nickel-titanium alloy or a cobalt-chromium alloy).

In some cases, as shown, prosthetic heart valve 100 includes three cultured cell leaflets 200. In some cases, prosthetic heart valves provided herein can have any suitable number of cultured cell leaflets, such as two, three, four, five, or more leaflets. In some cases, cultured cell leaflets 200 are secured to one another. In some cases, cultured cell leaflets 200 can be secured to one another by a suture (not shown) or a plurality of sutures. Cultured cell leaflets 200 can be sutured alongside edges of a body portion of each leaflet. In some cases, prosthetic heart valves provided herein can include a single line of sutures, which can be adapted to minimize leaks, minimize the width of a seam, and/or minimize the profile of a replacement heart valve during a percutaneous insertion. In some cases, prosthetic heart valves provided herein can include multiple lines of sutures.

In some cases, a sheet of cultured cells can be flattened. For example, a platen system can be used to flatten a sheet of cultured cells. In some cases, a frame can be used along with a platen to flatten cultured cells to further provide a more consistent thickness prior to fixation. The bottom plate can be sized to fit within the tissue fixation frame, and the top platen can be expanded to include a flat rectangular plate of the same size as the bottom platen. The top platen can be program controlled so that it will compress to a fixed thickness. Alternatively, spacers can be used to limit the travel of the moveable platen using a mechanical method.

Both achieve the same result, to limit the amount of travel of the movable platen to a fixed distance, thereby providing tissue of a fixed thickness. In some cases, the bottom platen could be the movable platen with the top platen fixed. The flattening process could occur at a separate station, as shown above, or be integrated into the BAT fixation device. Platen materials can be medical grade or food grade plastics or corrosion resistant stainless steel or other materials suitable for use in a corrosive environment while still permitting cleaning. In some cases, a highly polished and smooth stainless steel can be used as the platen surface to resist any transfer/imprinting of features (e.g., mold lines, machine lines, etc.) from the platen to the tissue.

Tissue-Only Sheets:

In some cases, leaflets provided herein can exclude exogenous materials. In some cases discussed below, biomaterial scaffolds can be used to product a composite leaflet material including the biomaterial scaffold and cultured cells. Tissue-only sheets can help circumvent eliciting an immune response, but the lack of an exogenous biomaterial scaffold means that the sheet must rely upon the cultured cells alone to provide an appropriate balance of mechanical integrity. As discussed below, cultured cell sheets provided herein, both with and without an exogenous biomaterial scaffold, provide the mechanical properties required for use as a leaflet in heart valves provided herein.

For example, tissue-only sheets were produced by having cells housed in standard cell culture conditions (37° C. and 5% CO2) and grown in standard growth media supplemented with 100 µM ascorbic acid. The cells reached confluence by one week, upon which the media was changed to experiment media conditions (Table 1, below). Experiment media was made fresh for each feeding and changed three times per week for all conditions. At 6 and 12 weeks, constructs were removed from culture and fixed in 0.6% glutaraldehyde for at least 24 hours prior to taking samples for analyses.

Composite Tissue Sheets:

In some cases, leaflets provided herein can include exogenous materials, such as biomaterial scaffolds. Biomaterial scaffolds can be made using any suitable material using any suitable technique. Electrospinning is one method used to generate fibrous polymeric mesh scaffolds, which can be used to mimic the ECM and serve as an attractive environment for cells. Material properties such as thickness, fiber diameter and alignment may be tuned to produce desired results. PLGA and PVDF are two polymers that have been successfully electrospun for biomedical applications and are currently FDA approved in various formats. PVDF is non-biodegradable, but has been shown to support cell growth. PLGA is a common bioresorbable material that is currently being used in multiple biomedical applications. Other types of scaffolds for composite tissue sheets are also contemplated.

Experimental Results

Tissue-only sheets and sheets including biomaterial scaffolds were developed using BDF, SMCs or BDF/SMC cocultures. Each condition was grown in duplicate for two different endpoints, as is detailed in Tables 1-3. At each endpoint, sheets were fixed in 0.6% glutaraldehyde. Small samples were taken for histological analyses of cell and ECM components, with collagen of particular interest. A minimum of two samples were taken for tensile testing in order to assess mechanical properties such as the ultimate strength.

For the tissue-only scaffolds, conditions with a single cell type (BDF only or SMC only) grown in growth media supplemented with ascorbic acid are considered baseline controls. For the tissue-polymer hybrid conditions, an additional set was maintained in identical conditions without cells.

TABLE 1

Tissue-Only Sheet conditions

| Condition | Cell Type | Media | Timepoints |
|---|---|---|---|
| Control | BDF SMC | DMEM, 10% FBS, 1% NEAA, 1% ANTI-ANT1, 100 µM AA | 6 weeks, 12 weeks |
| Coculture | 1:1 BDFs + SMCs | | |
| HG | BDF | HG DMEM, 10% FBS, 1% NEAA, 1% ANTI-ANTI, 100 µM AA | |
| CM | BDF | DMEM, 20% HPAFF II CM, 10% FBS, 1% NEAA, 1% ANTI-ANT1, 100 µM AA | |
| Copper | BDF | DMEM, 10% FBS, 1% NEAA, 1% ANTI-ANTI, 10 mM CuSO4, 100 µM AA | |
| Multiple sheets stacked after 3 weeks | BDF SMC | DMEM, 10% FBS, 1% NEAA, 1% ANTI-ANT1, 100 µM AA | |
| Bioreactor: feeding on top and bottom | 1:1 BDFs + SMCs | DMEM, 10% FBS, 1% NEAA, 1% ANTI-ANTI, 100 µM AA | 6 weeks |

TABLE 2

Tissue-PVDF Scaffold Hybrid

| | Scaffold Conditions | | | Culture Conditions | | |
|---|---|---|---|---|---|---|
| | PEG | | | | | |
| | Type | Plasma | Sinter | Cell Type | Media | Timepoints |
| Experiment | 1 | + | None | 1:1 BDFs + SMCs | DMEM, 10% FBS, 1% NEAA, 1% ANTI-ANTI, 100 µM AA | 5 weeks, 8 weeks |
| | 2 | + | 130° C. 20 min | | | |
| | 3 | + | 130° C. 20 min, 140° C. 15 min | | | |

TABLE 2-continued

Tissue-PVDF Scaffold Hybrid

| | | Scaffold Conditions | | | Culture Conditions | |
|---|---|---|---|---|---|---|
| | | PEG | | | | |
| | Type | Plasma | Sinter | Cell Type | Media | Timepoints |
| | 4 | − | None | | | |
| | 5 | − | 130° C. 20 min | | | |
| | 6 | − | 130° C. 20 min, 140° C. 15 min | | | |
| Controls | 1 | + | None | None | DMEM, 10% FBS, 1% NEAA, 1% ANTI-ANTI, 100 μM AA | 5 weeks, 8 weeks |
| | 2 | + | 130° C. 20 min | | | |
| | 3 | + | 130° C. 20 min, 140° C. 15 min | | | |
| | 4 | − | None | | | |
| | 5 | − | 130° C. 20 min | | | |
| | 6 | − | 130° C. 20 min, 140° C. 15 min | | | |

20

TABLE 3

Tissue-PLGA Scaffold Hybrid

| | | Scaffold Conditions | | | Culture Conditions | |
|---|---|---|---|---|---|---|
| | | Fiber | Fiber | | | |
| | Sample | Orientation | Diameter | Cell Type | Media | Timepoints |
| Experiment | 1 | Aligned | 1 μm | 1:1 BDFs + SMCs | DMEM, 10% FBS, 1% NEAA, 1% ANTI-ANTI, 100 μM AA | 5 weeks, 8 weeks |
| | 2 | | 5 μm | | | |
| | 3 | | 10 μm | | | |
| | 4 | Random | 1 μm | | | |
| | 5 | | 5 μm | | | |
| | 6 | | 10 μm | | | |
| Controls | 1 | Aligned | 1 μm | None | DMEM, 10% FBS, 1% NEAA, 1% ANTI-ANTI, 100 μM AA | 5 weeks, 8 weeks |
| | 2 | | 5 μm | | | |
| | 3 | | 10 μm | | | |
| | 4 | Random | 1 μm | | | |
| | 5 | | 5 μm | | | |
| | 6 | | 10 μm | | | |

Dermal fibroblasts and arterial smooth muscle cells were isolated using a technique known in the art. Cells were maintained in culture in standard conditions at 37° C. with 5% $CO_2$ in DMEM supplemented with 10% FBS, 1% NEAA, 1% anti-anti.

Tissue-only sheets were generated by seeding cells at 12,000 cells/$cm^2$ (BDFs, SMCs, or BDF/SMC 1:1 coculture) in 100 mm petri dishes. Circular thin frames were cut from cotton western blot transfer paper, placed into the cell culture dishes and weighted down using sterilized stainless steel hex nuts. The frames can provide structure to prevent the cell sheet from contracting, as well as a grip for handling the sheet without damaging the cells. These frames can be easily removed from the sheet if necessary.

Figure 7:
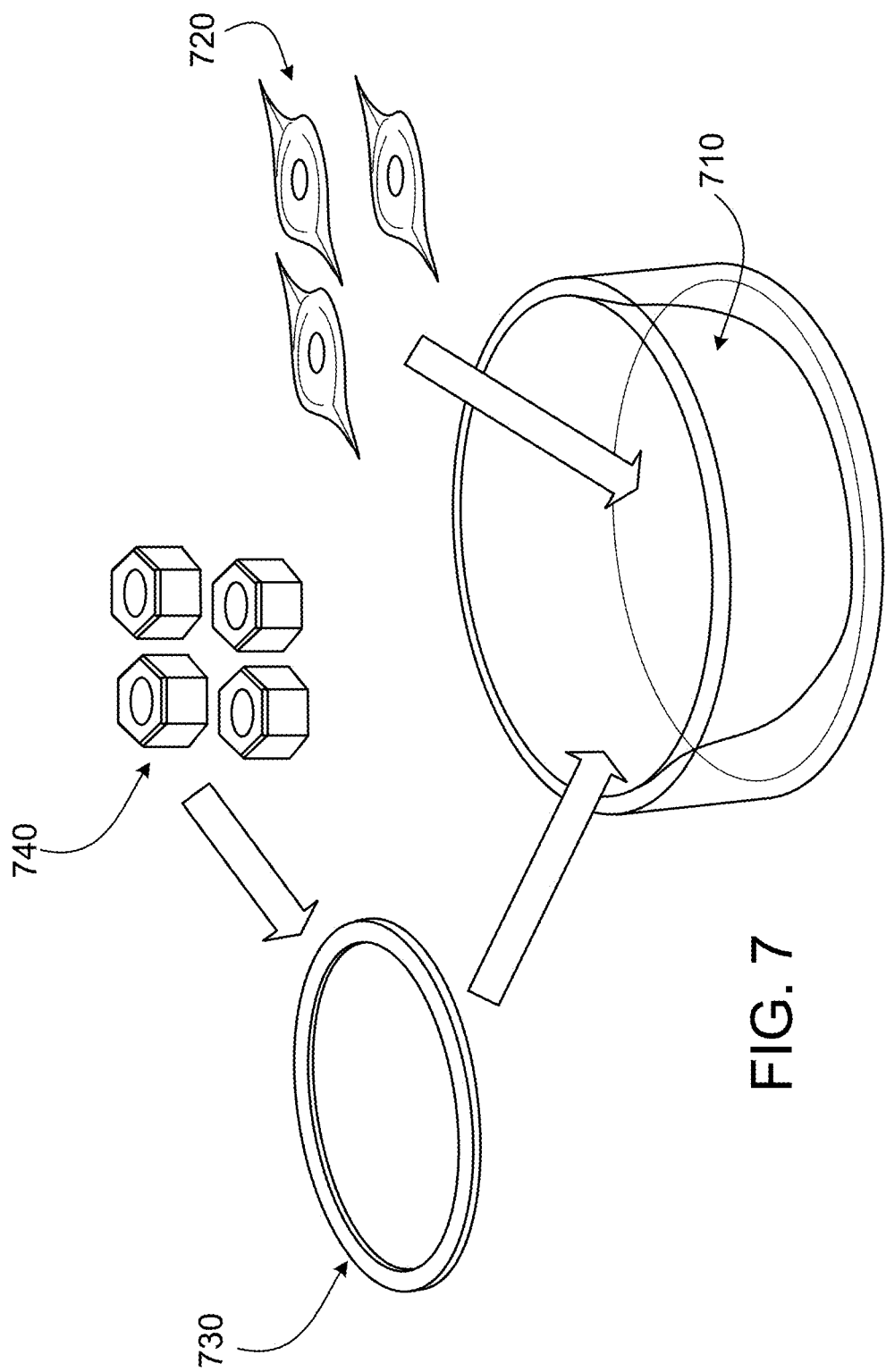
FIG. 7 depicts an exemplary setup for culturing a tissue-only sheet.

FIG. 7 illustrates a setup for culturing a tissue-only sheet. The setup includes a petri dish 710, cells 720, a paper frame 730, and hex nuts 740. Hex nuts 740 are used to weigh down paper frame 730. Paper frame 730 serves as a support for cells 720 that prevents the sheet from contracting as the sheet grows thicker, as well as provides a grip for handling upon removal from the plate.

Cells were housed in standard cell culture conditions (37° C. and 5% $CO_2$) and grown in standard growth media supplemented with 100 μM ascorbic acid. The cells reached confluence by one week, upon which the media was changed to experiment media conditions (Tables 1-3, above). Experiment media was made fresh for each feeding and changed three times per week for all conditions. At 6 and 12 weeks, constructs were removed from culture and fixed in 0.6% glutaraldehyde for at least 24 hours prior to taking samples for analyses. More detailed protocols are provided in Appendix C.

An additional condition labeled as "Bioreactor" was seeded with BDF/SMC 1:1 coculture and grown in the same manner described above in a 150 mm cell culture plate for three weeks. After three weeks, the tissue sheet was peeled from the plastic and transferred into a holding chamber that allowed media access to both sides of the scaffold. At six weeks of growth (three weeks in culture plastic and three weeks in the holding chamber), the sheet was removed and fixed in 0.6% glutaraldehyde for analyses.

Tissue-polymer scaffold sheets were made by cutting strips of PVDF and PLGA and placing them in uncoated petri dishes, weighing them down with sterile hex nuts, and presoaking them in growth media, removing the media, and seeding the cells. The strips were 0.5 inches wide. The PVDF strips were a minimum of 2 inches in length. The PVDF strips were autoclaved at 121° C. for 15 minutes prior to placement in the petri dishes. The PVDF strips were soaked in growth media for two hours, while the PLGA strips were soaked in growth media for 30 minutes. As per the manufacturer instructions, the PLGA strips were soaked in 70% ethanol for four hours and rinsed thoroughly in PBS in the petri dishes prior to being weighed down with the sterile hex nuts and soaked in the growth media. The PGLA strips having aligned scaffolds of the smallest diameter shrank immediately upon exposure to ethanol, and all material had been used up. The larger diameter aligned PGLA scaffolds shrank more slowly. New strips of PGLA were cut from remaining scaffolds and sterilized while flattened between two glass slides, as per manufacturer suggestion.

BDFs were seeded onto the strips at a high concentration (100,000 cells/ml) in small enough volumes to cover the strip without flooding into the plate. Cells were incubated for three hours and then excess media was carefully removed. The same process was repeated for SMCs. After three hours incubation, the dishes were flooded with 15 ml growth medium supplemented with 100 µM ascorbic acid.

Seeded scaffolds were housed in standard cell culture conditions (37° C. and 5% $CO_2$). Growth media was supplemented with 100 µM ascorbic acid immediately prior to each change, three times per week. Scaffolds were transferred to fresh non-treated plates each week to prevent cells from bridging attachments to the plastic. At 5 and 8 weeks, constructs were removed from culture and fixed in 0.6% glutaraldehyde for at least 24 hours prior to taking samples for analyses.

Test specimens of tissue only and tissue-polymer scaffold sheets were tested for tensile strength. Each test specimen for tensile testing was prepared by cutting strips to a size of 4.5×25 mm. The strips were placed in conical tubes containing pre-warmed PBS. These tubes were kept in a 37° C. water bath until immediately prior to testing. The thickness of each strip was measured using digital micrometers in three locations along the gauge length and entered into Excel. Excel was used to calculate the average thickness, to be entered when prompted into the Bluehill software. Digital calipers were used to measure the width of the samples and also entered into the software.

Figure 8:
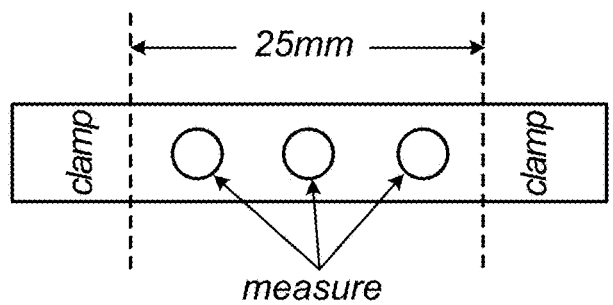
FIG. 8 depicts how a sample cell sheet is cut for tensile testing.

FIG. 8 illustrates how strips are cut for tensile testing. Thickness measurements were taken using digital micrometers at three points along the gauge length of the strip as indicated by red circles. Grip faces were modified by gluing fine grit sand paper in order to provide a better grip on the tissue specimens. The test strips were loaded into the pneumatic grips and set with a gauge length of 25 mm. Samples were stretched until a preload of 0.1 MPa. Data was captured beginning with pre-cycling (5 cycles from 0.1 MPa to 1.0 MPa) and ending at failure (defined as 80% peak load). Data collected was exported into Excel for analyses. Only test data starting at 0.1 MPa after 5 pre-cycles was used for analyses.

Biopsy punches were used to collect 10 mm diameter samples from each tissue or tissue-polymer hybrid sheet for histological analyses. After fixation in formalin, samples were loaded into histology cassettes for microwave tissue processing. Samples were placed in 100% ethanol and agitated and heated to 68° C. for four minutes. The ethanol was replaced with isopropyl alcohol and the samples were agitated and heated to 74° C. for four minutes. Cassettes were placed in preheated paraffin and microwaved at 80° C. for seven minutes.

After tissue processing, samples were cut in half to produce two semicircles. Each half was placed perpendicularly into a mold so that the flat edge was along the bottom. The samples were embedded in paraffin and then cooled in a −20° C. freezer in preparation for sectioning with a microtome. Paraffin embedded samples were kept cold, either in the freezer or on a cold plate, for sectioning. Sections 5 µm thick were cut and placed into DI water in a water bath set at 40° C. At least two sections per slide were floated onto the slides and air dried overnight. Prior to staining, slides were baked in a 60° C. oven overnight.

Masson's Trichrome and Russell-Movat Pentachrome stains were performed to assess the ECM components of each scaffold cross section. Slides were deparaffinized and rehydrated through a series of xylene and graded ethanol steps. Slides were stained, dehydrated, and coverslipped using EcoMount mounting media. Table 4 details the color scheme for each of the staining protocols.

TABLE 4

Guide to specific staining coloration for Masson's Trichrome and Russel-Movat Pentachrome.

|  | Masson's Trichrome | Russell-Movat |
| --- | --- | --- |
| Muscle Fibers | Red | Red |
| Fibrin | Pink | Red |
| Collagen | Blue | Yellow |
| Nuclei | Blue or Black | Black |
| Elastin | N/A | Black |
| Glycosaminoglycan | N/A | Blue |

Slides were visualized using an Olympus BX45 microscope and images were taken using an Insight Spot 6 camera and Spot 5.1 software. Images were collected of entire cross sections using 2× magnification and then spliced together using Photoshop. More detailed images were taken using the 40× magnification to collect representative samples within each cross section.

During analysis, the data presented in Table 5 below was excluded from the study for the reasons listed.

| Scaffold Type | Sample | Reason |
| --- | --- | --- |
| Tissue-only | BDF Control-6 week No. 3 SMC Control-12 week No. 2 SMC Control-6 week No. 1 Coculture-6 week No. 1 BDF HG-6 week No. 1 | Poor sample quality |
| Tissue-only | Copper-all samples | Cells died |
| Tissue-only | Layered scaffolds-all samples | Layers delaminated |
| Tissue-only | BDF CM-all samples | Constructs contracted before first endpoint |
| PVDF | PVDF 2-8 week Sample No. 1 (+cells) | Data is extreme outlier, possible calculation error |
| PLGA | All samples | Scaffolds curled and crumbled, unable to analyze |

Figure 9:
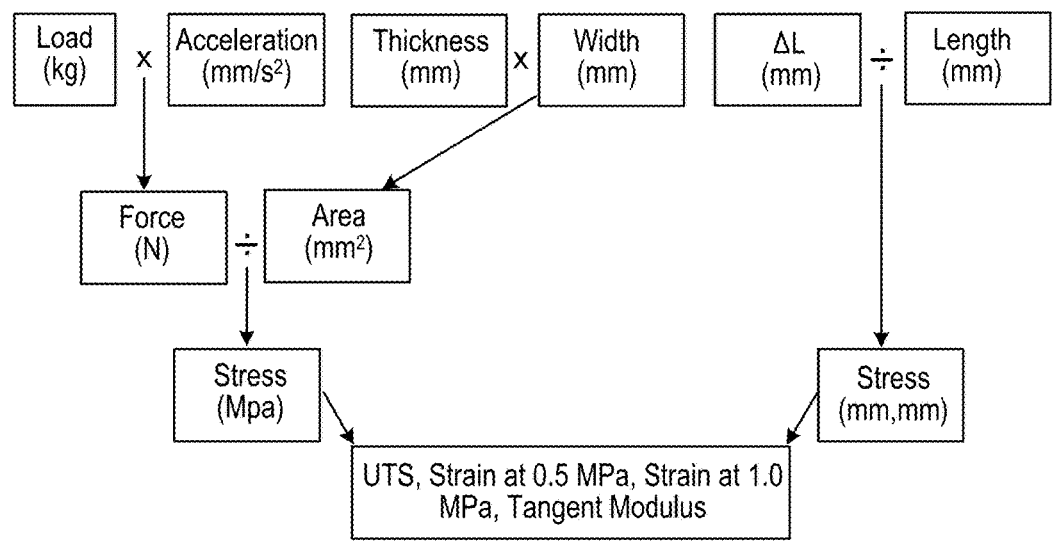
FIG. 9 illustrates how the stress and strain are calculated.

The Bluehill 2 software that was used to run the Instron mechanical tester collected data in real time of the change in length and load of the test specimen. Prior to testing each sample, the user input the sample dimensions: thickness, width, and gauge length. From this information, the software calculated the cross sectional area, which was also used to calculate force and stress data. FIG. 9 illustrates the data calculations used. As shown, the load, acceleration and ΔL represent parameters measured by the Bluehill software, while thickness and width are user entered parameters. Stress and strain data was exported into Excel, where further calculations were made. The region of physiological relevance and of particular interest to this study is between 0.5 MPa and 1.0 MPa. Table 6 details parameters used in this study. The "average" function in Excel was used to calculate the mean value of each group, and "stddev.p" function was used to calculate the standard deviation.

TABLE 5

Calculations performed using Excel to extrapolate information from stress and strain data

| Parameter | Calculation/Function |
|---|---|
| UTS | =Max( ) |
| Strain at 0.5 MPa | Search stress data and find corresponding strain value |
| Strain at 0.1 MPa | |
| Tangential Modulus | $= \frac{((\text{Stress at } 1.0 \text{ MPa}) - (\text{Stress at } 0.5 \text{ MPa}))}{((\text{Stress at } 1.0 \text{ MPa}) - (\text{Stress at } 0.5 \text{ MPa}))}$ |

Mechanical and histological analyses of the tissue-only scaffolds are presented below. One sample per time point was divided for analyses. A minimum of two test specimen were cut for mechanical testing of each sample.

It should be noted that BDF HG samples detached from the cell culture plates after three weeks and continued to float submerged in media, giving it access to media from both sides. The other conditions maintained contact with the tissue culture plastic until they were removed at the predetermined endpoints, allowing less media access to the bottom of the sheet as they grew thicker. There is histological evaluation but no mechanical data for this condition.

TABLE 6

Scaffold thickness (μm) as measured by digital micrometer at three different points along the length of each test specimen. Data was pooled for each sample group and is given as the mean and standard deviation.

| Sample type | Timepoint | Mean | Std Dev |
|---|---|---|---|
| BDFS-Control | 6 week (n = 2) | 81 | 3 |
| | 12 week (n = 4) | 132 | 8 |
| SMCs-Control | 6 week (n = 3) | 70 | 0 |
| | 12 week (n = 3) | 118 | 4 |
| BDF/SMC Coculture | 6 week (n = 3) | 126 | 5 |
| | 12 week (n = 4) | 198 | 6 |
| BDFs-High Glucose | 6 week (n = 3) | 89 | 3 |

TABLE 6-continued

Scaffold thickness (μm) as measured by digital micrometer at three different points along the length of each test specimen. Data was pooled for each sample group and is given as the mean and standard deviation.

| Sample type | Timepoint | Mean | Std Dev |
|---|---|---|---|
| | 12 week (n = 4) | 146 | 6 |
| SMCs-Conditioned Media | 6 week (n = 4) | 80 | 0 |
| | 12 week (n = 4) | 130 | 0 |

Figure 10A:
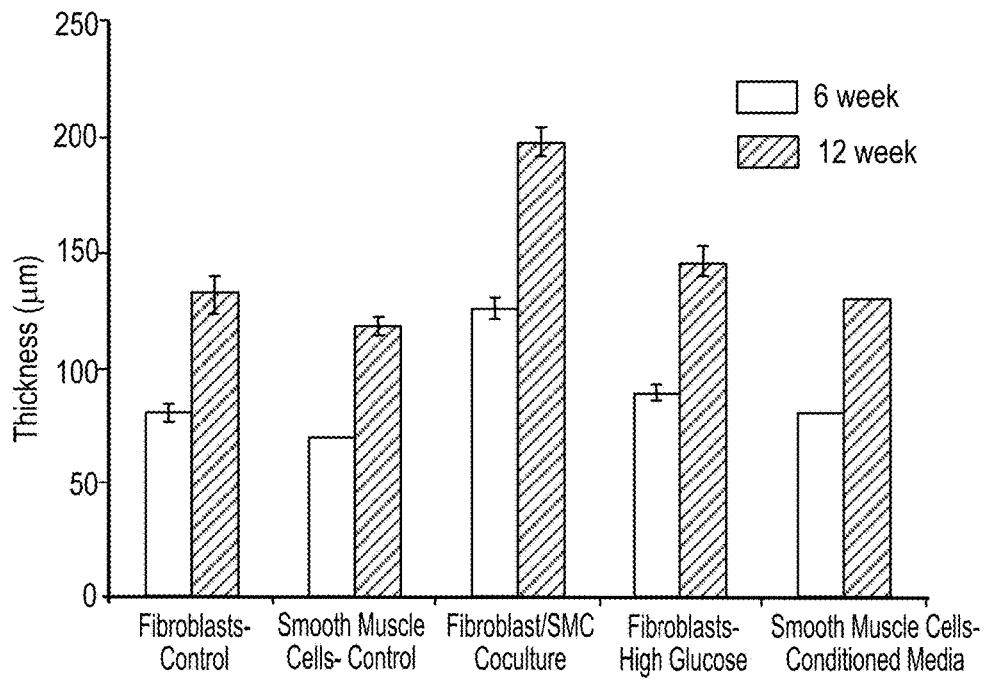
FIGS. 10A-10D show the properties of different cultured sheets.

FIG. 10A depicts the scaffold thickness (μm) as measured by digital micrometer at three different points per test specimen. Data was pooled for each sample group and is given as mean+/− standard deviation. All conditions show an increase in thickness from 6 weeks to 12 weeks, with the coculture conditions the thickest at each timepoint.

TABLE 7

UTS (MPa) determined as the highest stress recorded by the Bluehill software. Data was pooled for each sample group and is given as the mean and standard deviation.

| Sample type | Timepoint | Mean | Std dev |
|---|---|---|---|
| BDFs-Control | 6 week (n = 2) | 1.59177 | 0.32089 |
| | 12 week (n = 4) | 2.103805 | 0.24724 |
| SMCs-Control | 6 week (n = 3) | 2.387747 | 0.307671 |
| | 12 week (n = 3) | 2.576423 | 0.428006 |
| BDF/SMC Coculture | 6 week (n = 3) | 4.08366 | 0.396616 |
| | 12 week (n = 4) | 3.120055 | 0.100685 |
| BDFs-High Glucose | 6 week (n = 3) | 2.240327 | 0.334704 |
| | 12 week (n = 4) | 3.263908 | 0.381222 |
| SMCs-Conditioned Media | 6 week (n = 4) | 1.605633 | 0.126461 |
| | 12 week (n = 4) | 2.156613 | 0.273142 |

Figure 10B:
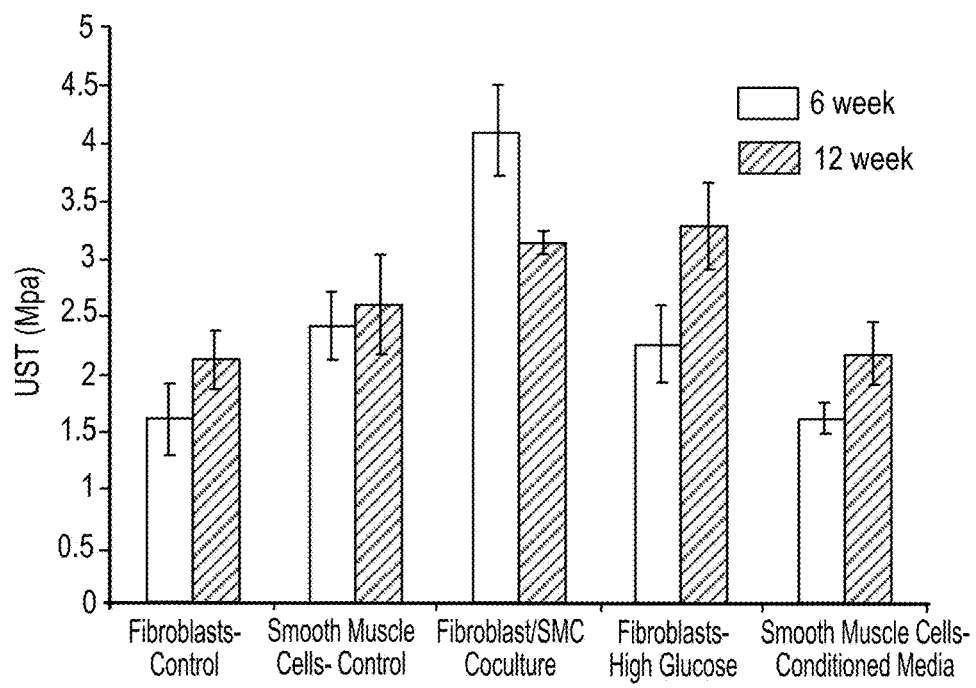

FIG. 10B depicts the ultimate tensile strength (UTS) in MPa from data pooled for each sample group and is given as mean+/− standard deviation. With the exception of the coculture condition, all samples showed increased strength from 6 to 12 weeks, following the same trend as the measured thickness. Coculture at 6 weeks showed the highest UTS measured overall, while BDF HG showed the highest UTS measured at 12 weeks.

TABLE 8

Strains measured at 0.5 MPa and 1.0 MPa, given as a %. Data is pooled for each sample group and is given as mean and standard deviation.

| Sample type | Timepoint | Strain at 0.5 MPa (%) | | Strain at 1.00 MPa (%) | |
|---|---|---|---|---|---|
| | | Mean | Std Dev | Mean | Std Dev |
| BDFS-Control | 6 week (n = 2) | 2.95 | 0.25 | 5.8 | 0.3 |
| | 12 week (n = 4) | 3.875 | 0.363146 | 7.025 | 0.511737 |
| SMCs-Control | 6 week (n = 3) | 3 | 0.648074 | 5.9 | 1.019804 |
| | 12 week (n = 3) | 3.533333 | 0.124722 | 6.366667 | 0.124722 |
| BDF/SMC Coculture | 6 week (n = 3) | 2.866667 | 0.124722 | 5.266667 | 0.124722 |
| | 12 week (n = 4) | 3.2 | 0.070711 | 5.75 | 0.15 |
| BDFs-High Glucose | 6 week (n = 3) | 2.866667 | 0.555778 | 5.4 | 0.828654 |
| | 12 week (n = 4) | 2.85 | 0.111803 | 5.425 | 0.204634 |
| SMCs-Conditioned Media | 6 week (n = 4) | 3.75 | 0.672681 | 7 | 1.046422 |
| | 12 week (n = 4) | 4.4 | 0.43589 | 7.7 | 0.6 |

Figure 10C:
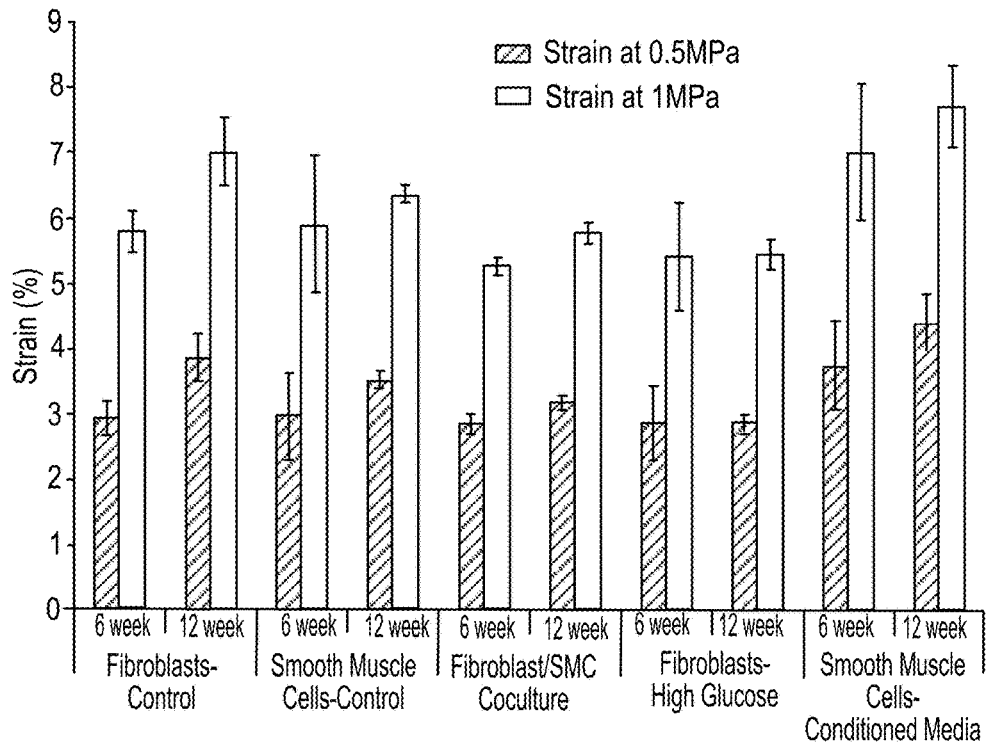

FIG. 10C depicts strain at 0.5 MPa and 1.0 MPa. Data is pooled for each sample group and is given as mean+/− standard deviation. All samples increased in stress measured from 6 to 12 weeks, showing an increase in elasticity. SMC CM conditions show the most elastic behavior.

TABLE 9

Tangential modulus (MPa), calculated as the slope between the two points at 0.5 MPa and 1.0 MPa. Data is pooled for each sample group and is given as mean and standard deviation.

| Sample type | Timepoint | Mean | Std Dev |
|---|---|---|---|
| BDFS-Control | 6 week (n = 2) | 18.03903 | 0.656552 |
| | 12 week (n = 4) | 15.94278 | 0.619592 |
| SMCs-Control | 6 week (n = 3) | 18.06628 | 2.413875 |
| | 12 week (n = 3) | 17.68103 | 0.240132 |
| BDF/SMC Coculture | 6 week (n = 3) | 20.96185 | 0.480832 |
| | 12 week (n = 4) | 19.78648 | 0.42325 |
| BDFs-High Glucose | 6 week (n = 3) | 20.30524 | 2.419884 |
| | 12 week (n = 4) | 19.86237 | 0.753046 |
| SMCs-Conditioned Media | 6 week (n = 4) | 14.30785 | 0.612216 |
| | 12 week (n = 4) | 15.52744 | 1.023712 |

Figure 10D:
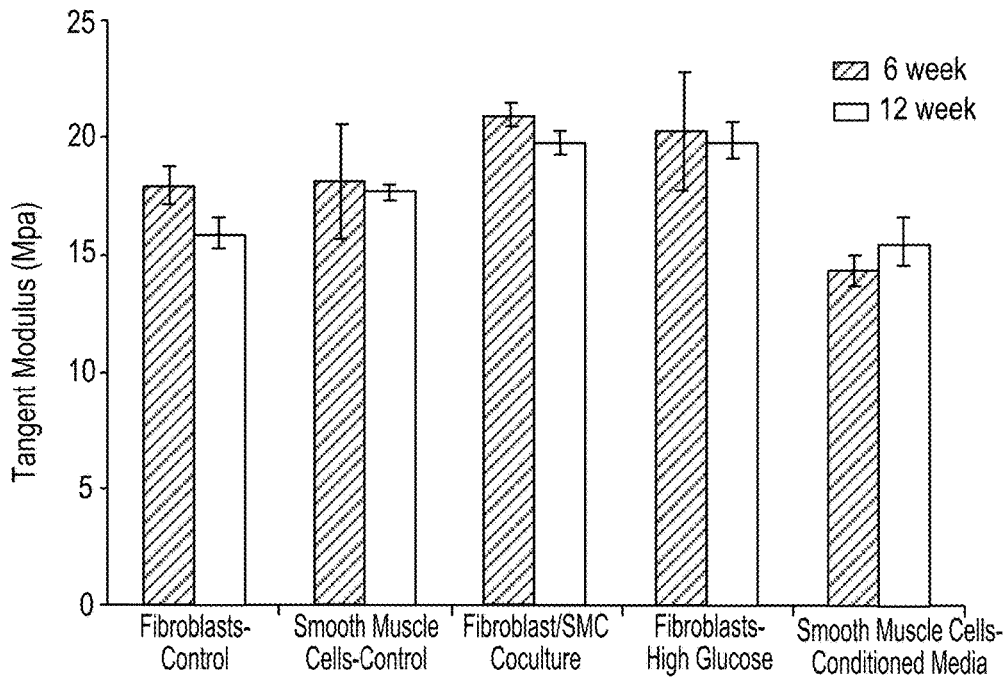

FIG. 10D depicts the tangential modulus (MPa), calculated as the slope between the two points at 0.5 MPa and 1.0 MPa. Data is pooled for each sample group and is given as mean+/− standard deviation. There is little change from 6 weeks to 12 weeks. The SMC CM shows the lowest modulus, thus the most elastic behavior of the group.

Figure 11A:
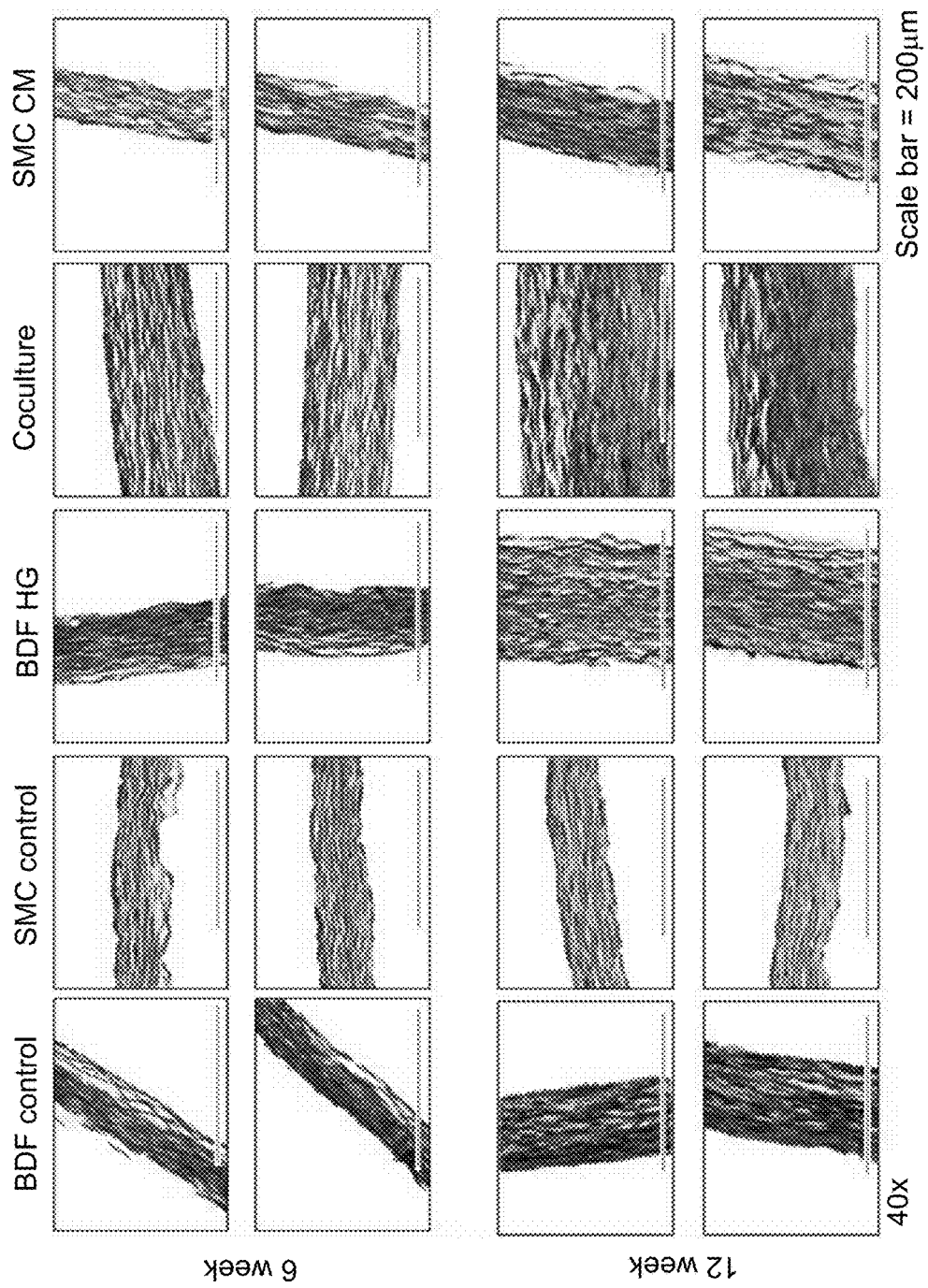
FIG. 11A shows representative 40× images of cross sections of tissue-only scaffolds stained for Masson's Trichrome.

FIG. 11A shows representative 40× images of cross sections of tissue-only scaffolds stained for Masson's Trichrome. More mature regions of the sheets show more collagen deposition, increasing from 6 weeks to 12 weeks. BDF HG samples at 12 weeks show more symmetrical staining, with collagen in the middle flanked by cell growth on each side, while the coculture condition at 12 weeks appears to show the most dense collagen deposition. Both SMC conditions show less collagen staining than the BDF or coculture conditions.

Figure 11B:
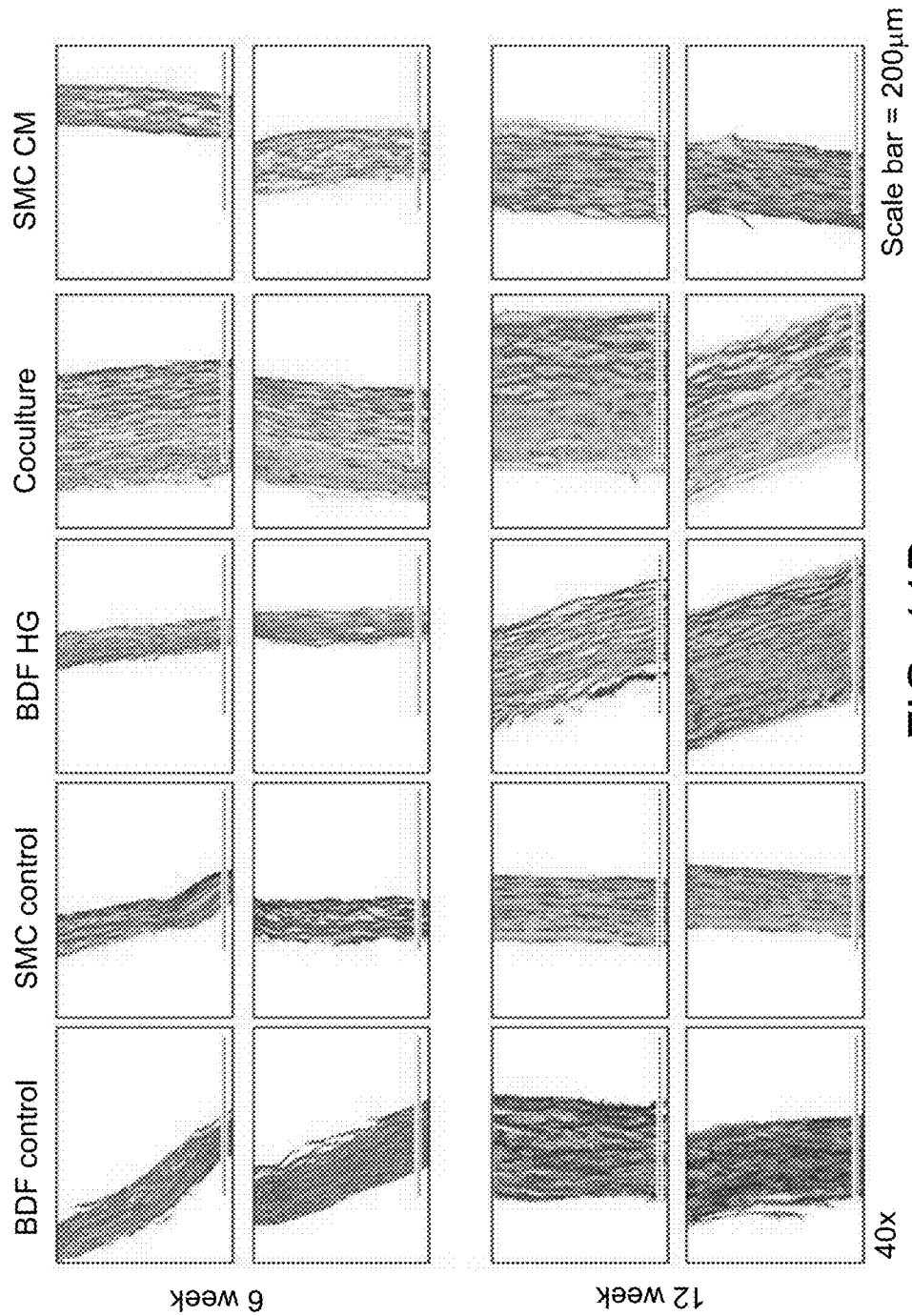
FIG. 11B shows representative 40× images of cross sections of tissue-only scaffolds stained for Russell-Movat Pentachrome.

FIG. 11B shows representative 40× images of cross sections of tissue-only scaffolds stained for Russell-Movat Pentachrome. The direction of growth of scaffolds goes from left to right, with the newest cell growth on the right hand side of each picture. More mature regions of the sheets show more collagen deposition, particularly in the 12 week time points. The SMC control and SMC CM at 12 weeks demonstrate production of glycosaminoglycans in addition to the collagen. BDF HG samples at 12 weeks show more symmetrical staining, with collagen in the middle flanked by cell growth on each side.

Figure 11C:
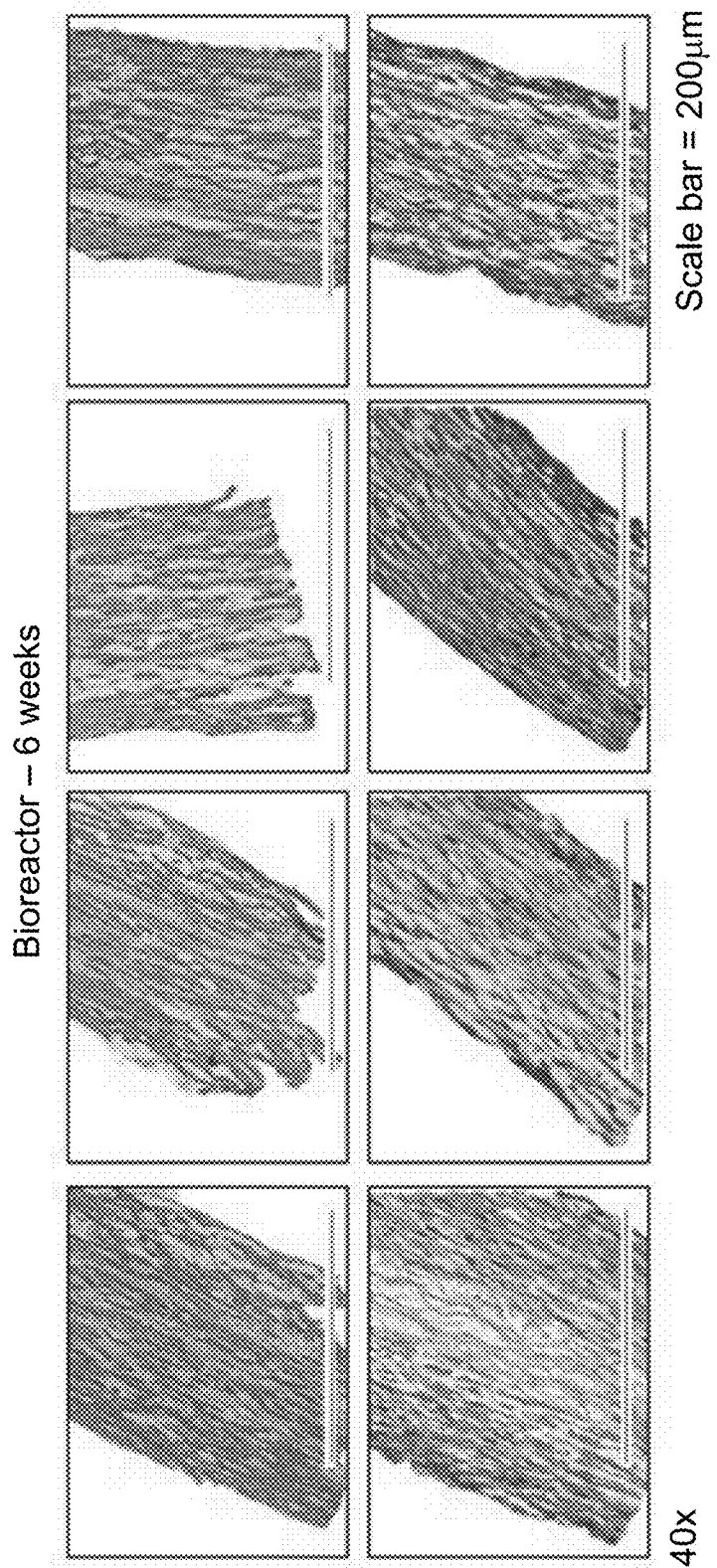
FIG. 11C shows tissue samples after growth in a bioreactor for 6 weeks, after 3 weeks feeding on both sides.

FIG. 11C shows tissue samples after growth in a bioreactor for 6 weeks, after 3 weeks feeding on both sides. The top row represents Russell-Movat Pentachrome staining and the bottom represents Masson's Trichrome. The access to media has helped to increase the thickness of the scaffold, however, there is not a substantial increase in collagen deposition. Both stains indicate greater symmetry of the cross section than the samples that were grown adhered to tissue culture plastic, indicating growth is taking place in both directions.

Tissue-only scaffolds were generated in vitro using BDFs, SMCs, and BDF/SMC 50:50 coculture. These cells were also subjected to different media supplements to support growth and collagen deposition. In all conditions, thickness and ECM production increased from six weeks to twelve weeks. Five conditions were successfully grown to achieve UTS>1 MPa. The coculture condition showed the greatest UTS at 6 weeks at 4.08+/−0.40, comparable to the tissue sheets produced by Cytograft (5.13+/−0.91). The BDF HG condition showed the highest strength at 12 weeks (3.26+/− 0.38) and second highest overall.

Although the general trend was that strength (UTS) increased with thickness, the two thickest sheets, coculture 12 weeks and bioreactor 6 weeks, were not measured to be the strongest. The coculture condition decreased in strength from the 6 to 12 week time points; the 12 week sheet demonstrated a more apparent gradient of collagen to cells from the bottom of the sheet to the top. Further analyses to measure enzyme activity would help determine whether MMPs (collagenases) are being secreted by the cells and degrading the collagen structure, affecting its properties over time. The bioreactor condition at 6 weeks more closely resembled the thickness of the 12 week coculture, showing an accelerated increase in thickness. This sheet consisted of a larger ratio of cells to collagen, and demonstrated the weakest mechanical properties of all conditions (UTS<1 MPa). The proportion of collagen to the overall thickness is likely a better indicator of material strength than thickness alone. Repeating this condition and growing to longer time points would show if collagen production increases over time and strength improves.

Access to media on both sides of the cell sheet increased thickness by allowing cells to continue to grow outward from both top and bottom sides, as demonstrated by the 12 week HG and 6 week bioreactor conditions. The BDF HG sheet lifted from the tissue culture plastic after three weeks, allowing better access to media on both sides. Histological staining supports that there is growth on both sides, as the cross sections show collagen in the center flanked by new cell growth on either side. The bioreactor condition, which was also fed on top and bottom after the third week, showed the same growth pattern. Whereas the BDF HG sheet floated in the media, the bioreactor condition was tethered in a holding chamber and media was supplemented on each side. Although the bioreactor condition was not subjected to any mechanical stimulation, inherent tension generated by suspending the sheet in the holding chamber may have been enough to alter ECM deposition, such as an increased production of stress fibers or an induction of alignment.

The SMC CM and BDF control conditions were the two weakest conditions at each time point. Russell-Movat staining showed that SMC CM samples had more GAG content than other conditions, which may contribute toward their more elastic behavior, as measured by the tangential modulus. The two stiffest conditions according to this measure were the coculture and BDF HG, also two of the thickest. Interestingly, the SMC control shows greater strength than the BDF control, but almost the same tangential modulus despite their different cell types and ECM compositions.

When overlaying the stress-strain curves, all conditions are similar within the initial toe regions, which include the area of interest between 0.5 MPa and 1.0 MPa, likely as collagen fibrils uncurled. Once the fibers are fully extended, the curves enter the linear region before 5% strain, where the slopes change to constant rates and the differences between conditions become more distinct. The BDF HG and culture stress-strain curves are nearly identical, as are the SMC and BDF controls. The SMC CM conditions have the shallowest slopes, and are the most elastic, while the BDF HG and coculture are the stiffest. There is not a visible distinction between time points within each group.

In order to accommodate more test conditions, replicates were limited to one per time point, limiting the sources of data. The conditions should be narrowed down and studies repeated for increased statistical significance. The coculture conditions showed more promising mechanical properties than either cell type alone, and HG media showed improved strength versus the other treatments. Coculture conditions should be tested with HG media to determine any increased benefits. Both sheet conditions comprised of SMCs as the single cell type stained positive for GAGs, while BDF conditions were predominately collagen. Changing the ratio of BDFs seeded versus SMCs may alter the properties of the scaffold by affecting the combination of EMC components secreted. Studying the effect of these two cell types in different ratios may allow the ability to tailor the mechanical properties of tissue sheets grown in vitro, thus expanding the potential applications for such a system.

Electrospun PVDF allowed cells to grow thick, collagen dense sheets on and around the surface. During tensile testing, these eventually delaminated into two distinct layers. Stress-strain curves (Appendix G) showed initial stiffer behavior as most of the resistance was provided by the cell layer. As the cell layer failed, there was a slight drop in stress until the load was picked up by the scaffold. The curves characterized by the cells on the scaffolds were comparable to the curves generated in the tissue only scaffolds: failure between 1 and 4 MPa at 15-20% strain. Variations in data are likely due to uneven cell coating, as some areas of the scaffolds were more densely populated with cells. True cross sections of the cell growth were more difficult to obtain, as the cells followed the contours of the material, growing in a more three-dimensional manner. As with the tissue-only sheets, scaffold conditions should be narrowed down to expand the number of replicates. The growth chamber used for the bioreactor condition may also be helpful to secure the scaffold and allow a flatter surface for increased consistency in cell growth.

Mechanical data suggests that tissue may be grown in vitro and generate extracellular matrix with quantifiable mechanical properties. Tissue-only sheets grown without exogenous scaffolds were grown with consistent properties that may be able to be manipulated further to meet desired characteristics. Further studies based off of these findings may be performed to enhance tissue properties by changing parameters such as cell type or media formulation. Better understanding of how to manipulate these properties may help expand the potential range of uses for this material.

Cell Only Cultured Sheet:

The following is the general protocol for setup of tissue engineered sheets using cells only. The cells are prepared according to the cell culture media protocols provided below. No exogenous scaffolds are used. Frames can be cut from gel blot transfer paper in order to provide enough structure to prevent the tissue sheets from contracting. The frames can be autoclaved ahead of time. Cells used are BDFs, SMCS, or 1:1 coculture of BDFs and SMCs. In some cases, other ratios of BDFs and SMCs can be used. In some cases, other cells are used. In order to prepare the plates for cell seeding, the frames are placed into p100 petri dishes as shown in FIG. 7 and presoaked in enough media to cover (the paper is very absorbent and this will help to flatten it prior to seeding cells); In some cases, aspirating excess media can help remove debris. Bolts can be placed on the paper to keep frame weighted down, avoiding overlap with the area inside frame. In some cases, the cells seeded are cells that have been grown and passaged at least once after thawing. The cells can be plated at 12,000 cells/cm$^2$ in growth medium (DMEM, 10% FBS, 1% NEAA, 1% anti-anti) supplemented with 100 uM ascorbic acid. In some cases, 1 week after seeding additional treatments can be added. The cells can be fed with glucose at regular intervals. The typical feeding schedule is three times per week, but high glucose conditions may need more frequent changes or additional media at later timepoints. In some cases, it takes a minimum of three weeks before the frames are able to be detached from the plate. In some cases, the frames are not detached until at least four weeks after being plated, especially for any applications that require difficult handling (i.e. rolling into tubes). After the frames are detached, weights may be removed. When lifting the sheets out of the plate, frames are less likely to detach from the cells if media is removed first. The sheet can be washed with PBS 2-3×, or until a pink color from media is no longer visible. The sheet can then be fixed in 0.6% glutaraldehyde solution at least overnight before preparing for analyses.

An additional condition labeled as "Bioreactor" was seeded with BDF/SMC 1:1 coculture and grown in the same manner described above in a 150 mm cell culture plate for three weeks. After three weeks, the tissue sheet was peeled from the plastic and transferred into a holding chamber that allowed media access to both sides of the scaffold. At six weeks of growth (three weeks in culture plastic and three weeks in the holding chamber, the sheet was removed and fixed in 0.6% glutaraldehyde for analyses.

Cell Culture Media Protocols:

The cell media protocols use a base media, which may be prepared ahead of time or prepared fresh. The following components can be combined and sterile filtered using vacuum flasks with 0.22 µm membranes to make the base media. A stock solution of 200 mM ascorbic acid can also be prepared ahead of time. In some cases, the stock solution of 200 mM ascorbic acid can be kept at 4° C. for up to three weeks. After three weeks, the stock solution of 200 mM ascorbic acid may be discarded due to loss of activity over time. The stock solution of 200 mM ascorbic acid can be added to the media immediately prior to use. When prepared ahead of time, the base media can include the components provided in Table 14. To prepare the ascorbic acid solution of 200 mM to be used at a final concentration of 100 uM, 579 mg of powder can be weighed out and dissolved in 10 ml of sterile water, and the solution filter sterilized into a 15 ml conical tube for storage at 4° C. To prepare a CuSO$_4$ stock solution of 200 mM to be used at a final concentration of 10 mM (20×), 24.97 g of powder can be weighed out and dissolved in 500 ml of sterile water, and the solution sterilized using a 500 ml filter unit and stored at 4° C. When prepared fresh, the base media can include the components provided in Table 15.

TABLE 14

Base Media

| Media | Components |
|---|---|
| Growth | DMEM, 10% FBS, 1% NEAA, 1% ANTI-ANTI |
| HG | HG DMEM, 10% FBS, 1% NEAA, 1% ANTI-ANTI |

TABLE 15

Experimental Media

| Media | Components |
|---|---|
| Control | Growth medium + 100 µM AA |
| CM | Growth medium + 20% HPAFF II CM + 100 µM AA |
| HG | HG medium + 100 µM AA |
| Copper | Growth medium + 10 mM CuSO4 + 100 µM AA |

General Cell Culture:

Cells, such as BDFs and SMCs, can be maintained using the cell culture media discussed above. In some cases, prior to seeding cells into experimental setups, cells can be maintained in vented cell culture T-flasks in growth medium. The medium can be changed regularly (e.g., three times per week) and cells can be passaged at approximately 80% confluency. The passaging protocol can include the steps of (a) detaching cells from plate with 0.25% trypsin-EDTA (SMCs typically detach quickly, at approximately 1 minute, while BDFs usually take 5-7 minutes, but may be longer depending on confluence), (b) avoiding harsh tapping or excessive agitation, which may make cells clump, (c) resuspending the cells in growth media (2× the volume of trypsin) and centrifuging at 150×g for up to 10 minutes, (d) aspirating supernatant and resuspending in fresh medium, A typical split is between 1:4 and 1:12 for routine passages. The cells can be incubated in standard conditions (e.g., 37° C., 5% $CO_2$). In some cases, cells may be counted and resuspended into desired concentration for experiment setup.

A number of embodiments of the invention have been described. Nevertheless, it will be understood that various modifications may be made without departing from the spirit and scope of the invention. Accordingly, other embodiments are within the scope of the following claims.

What is claimed is:

1. A prosthetic heart valve comprising
a plurality of leaflets secured together and retained within an expandable tubular member, the leaflets comprising radially or biaxially tensioned and chemically cross-linked cultured cell tissue;
wherein the radially or biaxially tensioned cultured cell tissue has been chemically cross-linked while under tension to prevent recoil of the cultured cell tissue after the tension is released; and
wherein the cultured cell tissue leaflets have a percentage of elongation at 500 kPa of between 6.5% and 8.5%.

2. The prosthetic heart valve of claim 1, wherein the cultured cell tissue is cultured from fibroblast cells.

3. The prosthetic heart valve of claim 2, wherein the fibroblast cells are dermal fibroblast cells.

4. The prosthetic heart valve of claim 3, wherein the dermal fibroblast cells are bovine dermal fibroblast cells.

5. The prosthetic heart valve of claim 1, wherein the cultured cell tissue is cultured from cells including smooth muscle cells.

6. The prosthetic heart valve of claim 5, wherein the smooth muscle cells are bovine smooth muscle cells.

7. The prosthetic heart valve of claim 1, wherein the cultured cell tissue is cultured from a mixture of fibroblasts and smooth muscle cells.

8. The prosthetic heart valve of claim 7, wherein the fibroblast cells and smooth muscle cells are in a ratio of between 20:80 and 80:20.

9. The prosthetic heart valve of claim 1, wherein the cultured cell tissue is cross-linked with glutaraldehyde.

10. The prosthetic heart valve of claim 1, wherein the cultured cell tissue is cultured for at least 3 weeks.

11. The prosthetic heart valve of claim 10, wherein cultured cell tissue is cultured for at least 5 weeks.

12. The prosthetic heart valve of claim 1, wherein the cultured cell tissue has a thickness of between 50 micrometers and 300 micrometers.

13. The prosthetic heart valve of claim 1, wherein the cultured cell tissue leaflets have a percentage of elongation at 1 MPa of between 10.5% and 13.5%.

14. The prosthetic heart valve of claim 1, wherein the cultured cell tissue leaflets have an ultimate tensile strength of between 4 MPa and 6.5 MPa.

15. The prosthetic heart valve of claim 1, wherein the cultured cell tissue leaflets have a moisture content of between 80% and 88%.

16. The prosthetic heart valve of claim 1, wherein the cultured cell tissue leaflets consist of radially or biaxially oriented and fixed cultured cell tissue.

17. A prosthetic heart valve comprising
a plurality of leaflets secured together and retained within an expandable tubular member, the leaflets comprising radially or biaxially tensioned and chemically cross-linked cultured cell tissue;
wherein the radially or biaxially tensioned cultured cell tissue has been chemically cross-linked while under tension to prevent recoil of the cultured cell tissue after the tension is released; and
wherein the cultured cell tissue leaflets have a shrinkage temperature of between 83.8° C. and 84.6° C.

18. A prosthetic heart valve comprising
a plurality of leaflets secured together and retained within an expandable tubular member, the leaflets comprising radially or biaxially tensioned and chemically cross-linked cultured cell tissue;
wherein the radially or biaxially tensioned cultured cell tissue has been chemically cross-linked while under tension to prevent recoil of the cultured cell tissue after the tension is released; and
the leaflets comprising tissue-only cultured cell tissue excluding exogenous biomaterial scaffolds.

* * * * *